US009017998B2

(12) United States Patent
Tarunina et al.

(10) Patent No.: US 9,017,998 B2
(45) Date of Patent: Apr. 28, 2015

(54) VESSEL FOR CULTURING CELLS

(75) Inventors: Marina Tarunina, Orpington (GB); Yen Choo, London (GB); Mylvaganam Jeyakumar, London (GB); Martin Arthur Town, London (GB); Diana Hernandez-Jaramillo, London (GB); Christopher James Johnson, London (GB)

(73) Assignee: Plasticell Ltd., London (GB)

( * ) Notice: Subject to any disclaimer, the term of this patent is extended or adjusted under 35 U.S.C. 154(b) by 19 days.

(21) Appl. No.: 13/371,543

(22) Filed: Feb. 13, 2012

(65) Prior Publication Data

US 2012/0208273 A1  Aug. 16, 2012

Related U.S. Application Data

(63) Continuation-in-part of application No. PCT/EP2010/004976, filed on Aug. 13, 2010.

(30) Foreign Application Priority Data

Aug. 13, 2009 (GB) .................................. 0914195.3

(51) Int. Cl.
| C12M 1/22 | (2006.01) |
| C12M 3/00 | (2006.01) |
| C12M 3/06 | (2006.01) |
| C12M 1/00 | (2006.01) |
| B01L 3/00 | (2006.01) |
| C12M 1/32 | (2006.01) |

(52) U.S. Cl.
CPC .............. *C12M 27/16* (2013.01); *B01L 3/5085* (2013.01); *C12M 23/12* (2013.01); *C12M 23/10* (2013.01); *C12M 23/34* (2013.01)

(58) Field of Classification Search
CPC ...... C12M 27/16; C12M 23/10; C12M 23/12; C12M 23/34; C12M 1/20; C12M 1/22; B01L 13/5085
USPC ................ 435/243, 297.1, 325, 366; 422/560
See application file for complete search history.

(56) References Cited

U.S. PATENT DOCUMENTS

| 5,460,945 A * | 10/1995 | Springer et al. ............. 435/7.24 |
| 6,987,019 B1 | 1/2006 | Rogalsky |
| 2004/0029267 A1 * | 2/2004 | Martin et al. ............. 435/299.1 |
| 2004/0110274 A1 | 6/2004 | Feygin |

(Continued)

FOREIGN PATENT DOCUMENTS

| JP | 7-504570 | 5/1995 |
| WO | WO 93/18132 | 9/1993 |
| WO | WO 98/27195 | 6/1998 |

(Continued)

*Primary Examiner* — Michael Hobbs
(74) *Attorney, Agent, or Firm* — Vedder Price P.C.; Thomas J. Kowalski; Rebecca G. Rudich

(57) ABSTRACT

The present invention provides an apparatus for culturing cells which may comprise two or more culture compartments and a pooling compartment, wherein each of said two or more culture compartments may be separated from the other culture compartments; each of said two or more culture compartments which may comprise a port for the addition or removal of medium; and the pooling compartment communicates with said two or more culture compartments. The present invention also relates to a stand for apparatus for culturing cells.

11 Claims, 22 Drawing Sheets

(56) References Cited

U.S. PATENT DOCUMENTS

2007/0031963 A1 2/2007 Chang et al.
2008/0176318 A1 7/2008 Wilson et al.

FOREIGN PATENT DOCUMENTS

| | | |
|---|---|---|
| WO | WO 2004/031369 | 4/2004 |
| WO | WO 2008/073313 | 6/2008 |

* cited by examiner

VESSEL FOR CULTURING CELLS

RELATED APPLICATIONS AND INCORPORATION BY REFERENCE

This application is a continuation-in-part application of international patent application Serial No. PCT/EP2010/004976 filed Aug. 13, 2010, which published as PCT Publication No. WO 2011/018234 on Feb. 17, 2011, which claims benefit of British patent application Serial No. 0914195.3 filed Aug. 13, 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention broadly relates to a cell culture vessel suitable for the culture of cells, and especially for culture protocols which may require repeated splitting and pooling of cultures for exposure to different conditions. Cells which may be cultured include, but are not limited to, animal cells, plant cells, groups of cells (including whole organisms), primary cells, cell lines, pluripotent cells, totipotent cells and stem cells.

BACKGROUND TO THE INVENTION

Over recent years cell culture has become a core technology in the life sciences. Cell culture is described in 'Basic Cell Culture' Oxford University Press (2002) Ed. J. M. Davis; and 'Animal Cell Culture' Oxford University Press (2000) Ed. John R. W. Masters; both of which are incorporated herein in their entirety by reference. Cell culture provides the basis for studying cellular processes such as the viability, phenotype, genotype, proliferation and differentiation of cells, and the formation of biological molecules, intermediates and products. It has also provided the means to study the regulation of these processes, from the genetic level-whether in isolation or in whole transgenic animals-down to the level of individual protein molecules.

Notwithstanding its enormous contribution to the current state of biology, in many respects cell culture remains a developing discipline, albeit an unusually exciting science ultimately offering the possibility of genetic therapy and tissue engineering. An important goal of cell culture is to be able to grow a wide variety of cells in vitro. The list of different cell types that can be grown in culture is extensive (see American Type Culture collection, http://www.atcc.org; European Collection of Cell Cultures, http://www.ecacc.org.uk; Deutsche Sammlung von Mikroorganismen and Zellkulturen GmbH, http://www.dsmz.de), includes representatives of most cell types, and is continually increasing as more and more culture conditions are discovered.

Despite the steady progress in the field, until recently the method of determining suitable culture conditions for new cell types has remained totally empirical: growth conditions are almost always discovered by trial and error. The choice of starting point will often be based on what was previously used by others for similar cells, or even what is currently being used in the laboratory for different cells. Many times these will simply be completely inadequate, and a process of trial and error must begin anew. Even when new culture conditions are successful, it is worthwhile remembering that adaptations of previous protocols will have introduced a historical bias to the experiment. For instance, much of the early tissue culture experiments made extensive use of fibroblasts, and to this date most standard cell culture conditions favour growth of cells derived from the mesoderm (fibroblasts, endothelium, myoblasts). The development of selective growth media for epithelial and other cell types based on these conditions was a challenge. For some of these cell types it is now known that serum—a normal component of many culture media for mesodermal cells-actually inhibits growth.

Applicants have previously described methods for developing suitable culture conditions, which allow for the viability, proliferation or growth, and retention of the phenotype of particular cell types. Some common problems, which are still encountered in cell culture, are the limited lifespan of primary cell lines, the change of characteristics of cell lines with passage, and their transformation accompanied by loss of interesting cellular characteristics. These effects severely limit the utility of cultured cells for use in experiments or assays.

Improved techniques for culturing cells and methods for discovering and implementing techniques for regulation of cellular processes such as growth, differentiation, metabolic activity, and phenotypic expression are presented in Applicants' international application WO 2004/031369. According to the procedures described therein, "units" of cells, which comprise one or more cells cultured, for example, on a bead, are subjected to different growth conditions in a combinatorial split-pool procedure, which involves repeated splitting and re-pooling of cell cultures, to expose different cell units therein to different culture conditions.

When handling large numbers of cell units, their identity and/or cell culture history (for example, the chronology and the exact nature of a series of culture conditions that any one group or unit may have been exposed to) can become confused. WO2004/031369 describes improved methods for determining the identity and/or cell culture history of cell units.

In WO2007/063316, Applicants describe methods for determining the activity of agents which act on a cell, using the split-pool procedure.

In WO2007/023297, Applicants describe further improved methods for tagging cells in split-pool cell culture experiments, better to determine which reagents and nutrients a cell has been exposed to in achieving a particular state.

The performance of split-pool cell culture experiments, however, is manually laborious and time-consuming, requiring iterative transfer of cell units between culture vessels and optionally between filtering devices and culture vessels. The transfer of cell cultures in between individual vessels for filtering, pooling, splitting and subsequent rounds of the same moreover potentially exposes the cultures to infectious agents and other sources of contamination. There is therefore a need for a cell culture vessel in which split-pool culture can be conducted easily, without the need to transfer the culture continuously between vessels.

Citation or identification of any document in this application is not an admission that such document is available as prior art to the present invention.

SUMMARY OF THE INVENTION

In accordance with a first aspect of the present invention, there is provided an apparatus for culturing cells which may comprise two or more culture compartments and a pooling compartment, wherein: each of said two or more culture compartments may be separated from the other culture compartments; each of said two or more culture compartments may comprise a port for the addition or removal of medium; and the pooling compartment communicates with said two or more culture compartments.

The invention therefore provides a single vessel which may comprise multiple culture compartments, in which cultures of cell units may be exposed to differing culture conditions in isolation. The vessel moreover may comprise means for mixing the cell cultures, by pooling; and for re-splitting the pooled culture into separate cultures of cell units, which may again be subject to differing culture conditions.

Each separate compartment for culturing the separate cultures of cell units may comprise a port for addition and/or removal of medium, nutrients, reagents, factors and the like. The ports in the culture compartments, and optionally the pooling compartment, advantageously may comprise a filter. The filter preferably permits the removal of liquid media and optionally any excess tags whilst retaining the cell units of interest within the compartment. In a preferred embodiment, cell units may comprise a plurality of cells and the filter allows the removal of the typically dead cells which have become detached from the cell units.

Preferably, the two or more cultures are pooled by being transferred from the separate culture compartments into a pooling compartment. The pooling compartment optionally also may comprise a port for the addition and/or removal of medium, nutrients, reagents, factors and the like.

Advantageously, tilting the vessel towards the pooling compartment causes the cell cultures to flow from the culture compartments into a pooling compartment, where they may mix; and tilting the vessel towards the culture compartments causes the cell culture to flow into the culture compartments, thus creating separate cell cultures.

Advantageously, the vessel may comprise one or more further routes, in addition to the ports mentioned above, through which media may be added to the cultures, or removed therefrom. For example, part of the vessel may be substantially open, optionally covered by a dust shield or lid, which may be movable or removable.

In one embodiment, there is provided an apparatus for culturing cells, which may comprise a plurality of culture compartments, isolated from one another by a separator wall, at least two of said culture compartments being joined to a pooling compartment at one end of said culture compartments; such that, when the apparatus may be tilted in the direction of the pooling compartment, culture medium flows from the parallel compartments into the pooling compartment, and media from said two or more compartments are pooled; and when the apparatus may be tilted in the direction of the culture compartments, culture medium in the pooling compartment may be divided into said two or more culture compartments, separated by the separator wall; and wherein each culture compartment may comprise a port for the addition or removal of medium.

In a further embodiment, the culture compartments may be arranged substantially parallel with each other in the vessel.

In a further embodiment, the pooling compartment may comprise features to aid the facile and thorough mixing of cell units, for example features that cause turbulent flow of liquid.

In a further embodiment, the device may contain features that allow handing by a robotic device, for example a feature that may be grasped by a robotic arm or held by a stand.

In a further embodiment, the device may contain an asymmetric external feature—such as a fin, to ensure the correct device orientation when grasped by a robotic arm or held by a stand.

In one embodiment the device may be shaped such that it may be possible for it to be placed upright on a surface. In another embodiment the device may be provided with a holder or rack which allows the device to stand upright on a surface.

The apparatus may be constructed from any suitable material. For example, a material selected from the group consisting of polyethylene, polypropylene, polyvinylchloride, polycarbonate, polystyrene, polyester, nylon, aramid polymers, polytetra fluoro ethylene (PTFE) and a metal or glass, or combinations thereof may be used. Exemplary metals include, for instance, stainless steel, titanium and aluminium. Preferably, the culture vessel of the invention may be non-toxic to cell culture and does not cause cells, cell units based on microcarriers and tags used to label cells and cell units to adhere to its surfaces.

Optical transparency may be an advantage in cell culture vessels, so transparent materials are particularly indicated.

In a second aspect, there is provided a method for repeated splitting and pooling of a culture of cells, which may comprise the steps of: (a) providing one or more cultures of cells and distributing the cultures between two or more culture compartments of an apparatus according to any preceding aspect or embodiment; (b) optionally, adding and/or removing one or more media reagents, which may be the same or different, to or from one or more of said two or more compartments, and/or culturing the cells; (c) pooling the cell cultures in the pooling compartment, to create a pooled cell culture; (d) splitting said pooled cell culture by distributing the pooled culture into the culture compartments; and (e) optionally, repeating one or more of steps (b)-(d).

Advantageously, the method further may comprise the step of isolating the cells from one or more of said compartments.

Steps (c) and (d) may be performed as part of step (a) to distribute the cultures between two or more culture compartments when they are first introduced into the apparatus. Preferably, however, steps (c) and (d) are performed after step (a). Step (c) may comprise pooling the cell cultures distributed in step (a) by transferring the cultures from the culture compartments into the pooling compartment to create a pooled cell culture.

A media reagent may be added and subsequently removed in optional step (b), for example to perform a washing round. The step of culturing the cells may be performed independently of the step of adding and/or removing one or more media reagents.

Optional step (e) may comprise repeating only step (b); repeating only steps (c) and (d); or repeating each of steps (b)-(d). Steps (c) and (d) may be completed before or after step (b). The steps may be repeated once or may be repeated several times.

The step of culturing the cells may be performed independently of the addition and/or removal of one or more media reagents. In other words, the step of culturing the cells may be performed without adding and/or removing media reagent. Conversely, the step of adding and/or removing the media reagent may be performed without culturing the cells.

The step of culturing the cells may comprise the following sub-steps: (i) transferring the cells from said two or more compartments to one or more different containers; (ii) culturing the cells in said one or more containers; and (iii) optionally, returning the cells to an apparatus according to any aspect or embodiment of the invention described herein.

Alternatively, the step of culturing the cells may comprise culturing the cells in said two or more compartments of the apparatus.

The step of culturing the cells may include incubating the cells.

Viewed from a further aspect, there is provided a method for repeated splitting and pooling of a culture of cells, which may comprise the steps of: (a) providing one or more cultures of cells and distributing the cultures between two or more culture compartments of an apparatus according to any preceding aspect or embodiment; (b) optionally, adding or removing one or more media reagents, which may be the same or different, to or from one or more of said two or more compartments, and culturing the cells; (c) pooling the cell cultures in step (a) by transferring the cultures from the culture compartments into the pooling compartment, to create a pooled cell culture; (d) splitting said pooled cell culture by distributing the pooled culture into the culture compartments; and (e) optionally, repeating steps (b)-(d).

In a further aspect, there is provided a kit which may comprise at least one vessel as set forth in the first aspect of the present invention, microcarriers of one or more types, and tags for labelling cells and/or microcarriers. Optionally, the kit may also comprise cells and data analysis software.

Viewed from a still further aspect, the present invention relates to a stand for apparatus, the stand which may comprise support means for supporting the apparatus in a first orientation. The support means may be suitable for supporting the apparatus in at least first and second orientations, wherein said first and second orientations may be angularly offset from each other. The apparatus may be preferably of the type described herein. The stand described herein is believed to be independently patentable.

The stand may be adapted to hold the apparatus in two orientations. The first orientation may be an upright position with the apparatus arranged substantially vertical (i.e. with the ports facing upwards). This upright position may be suitable for the addition and removal of bead suspensions. The second orientation may be at an angle of 45 degrees from the vertical. This inclined position may be suitable for allowing the user to easily backwash stuck beads from the inside of the filter after a wash step. Preferably, in both positions the beads may be separated in the separate culture compartments. It will be appreciated that the support means may be adapted to support the apparatus in more than two orientations.

The stand preferably may comprise a first pair of cooperating slots or recesses for supporting the apparatus in said first orientation and a second pair of cooperating slots or recesses for supporting the apparatus in said second orientation. The slots may be preferably each adapted to receive a projection provided on the apparatus. Alternatively, the stand may comprise a pair of projections locatable in a first pair of slots or recesses formed in the apparatus to support the apparatus in said first orientation, the projections being locatable in a second pair of slots or recesses formed in the apparatus to support the apparatus in said second orientation.

In an alternative arrangement, the support means may be adapted movably to support the apparatus and enable it to be moved from said first position to at least said second position. For example, the support means may comprise a pivotably mounted cradle or holder for pivotably supporting the apparatus. At least in preferred embodiments, the apparatus may be smoothly rotated between said first and second orientations. Thus, the orientation of the apparatus may be continuously variable. In use, the apparatus may be positioned in different pool, split and wash orientations. A locking device may be provided to lock the apparatus in a desired orientation. The stand may also contain a waste tray to capture liquid from the apparatus, for example liquid drained during a wash step. In use, the movable holder may be rotated to take the device through a split-pool-split sequence in addition to the described first and second positions.

The apparatus may be coupled to a stand (either permanently or semi-permanently). At least in preferred embodiments, however, the apparatus may be removed from the stand.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
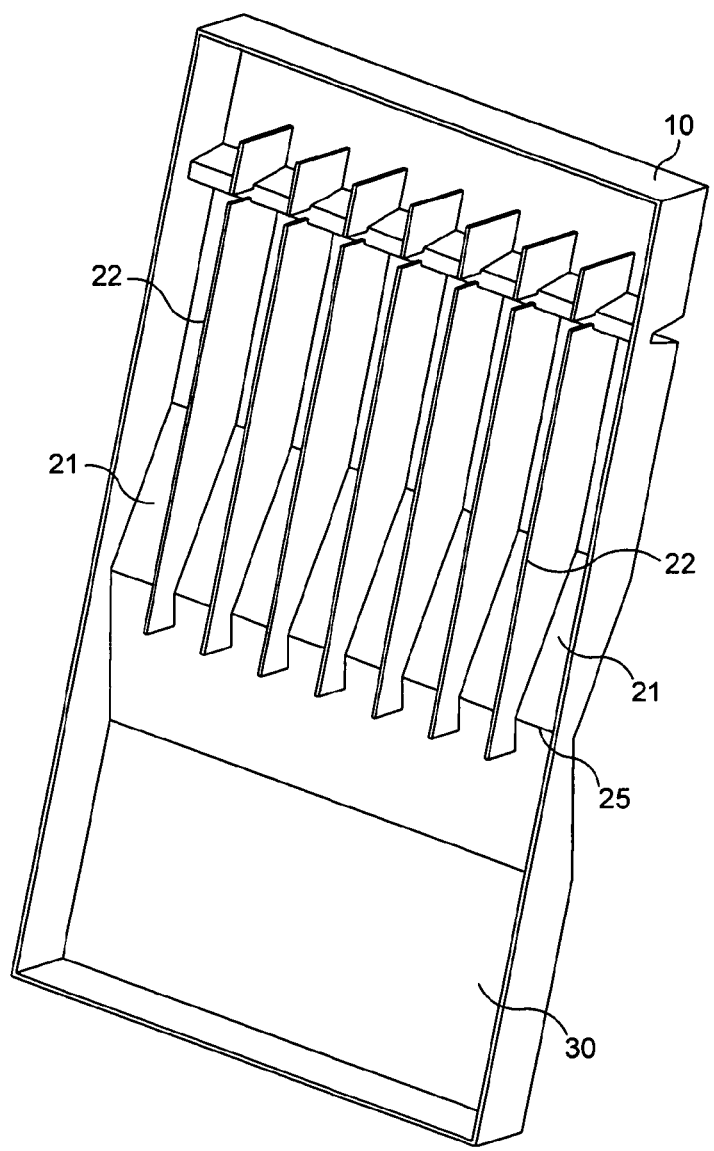
FIG. 1 is a perspective view of one embodiment of the apparatus of the present invention.

As used herein, the term "culture conditions" refers to the environment which cells are placed in or are exposed to in order to promote growth or differentiation of said cells. More particularly, the term refers to culture media and specific agents which may be incorporated into culture media and which may influence the growth and/or differentiation of cells.

A cell, as referred to herein, is defined as the smallest structural unit of an organism that is capable of independent functioning, or a single-celled organism, consisting of one or more nuclei, cytoplasm, and various organelles, all surrounded by a semipermeable cell membrane or cell wall. The cell may be prokaryotic, eukaryotic or archaebacterial. For example, the cell may be a eukaryotic cell. Mammalian cells are preferred, especially human cells. Cells may be natural or modified, such as by genetic manipulation or passaging in culture, to achieve desired properties. A stem cell is defined in more detail below, and is a totipotent, pluripotent or multipotent cell capable of giving rise to more than one differentiated cell type. Stem cells may be differentiated in vitro to give rise to differentiated cells, which may themselves be multipotent, or may be terminally differentiated. Cells differentiated in vitro are cells which have been created artificially by exposing stem cells to one or more agents which promote cell differentiation. Where appropriate, the term "cell" may also include a group of cells growing on or in a microcarrier, also referred to as a "cell unit".

A group of cells, which may be a group of one. Pools of cell units may be sorted, subdivided and handled without substantially dissociating the cell units themselves, such that the cell unit behaves as a colony of cells and each cell in the cell unit is exposed to the same culture conditions. For some embodiments, a cell unit may comprise a microcarrier or bead to which is adhered a group of cells.

A totipotent cell is a cell with the potential to differentiate into any type of somatic or germ cell found in the organism. Thus, any desired cell may be derived, by some means, from a totipotent cell.

A pluripotent cell is a cell which may differentiate into more than one, but not all, cell types. Examples of pluripotent cells are blastocyst-derived stem cells, or induced pluripotent stem cells (iPS cells).

In one aspect, the term "tag", as used herein, refers to any tag that is used to identify a cell unit and/or determine a culture condition, or a sequence of culture conditions, to which the cell unit has been exposed. In another aspect, the term "tag" refers to any tag that is added to a cell unit as a means of specifically labelling that cell unit, thus facilitating the identification of a cell unit and/or the determination of a culture condition and/or a sequence of culture conditions, to which the cell unit has been exposed. Suitably, the tag exists in a number of related but distinct variants which are easily distinguishable, as described in further detail herein. The tag typically forms part of a complex with a microcarrier. For some embodiments, the tag is a sphere or a bead—such as a microsphere or a microbead. For some embodiments the tag is a rod-shaped particle—such as a nanowire. As referred to herein, the term "tag" is synonymous with the term "label".

Exposure to culture conditions A cell is exposed to culture conditions when it is placed in contact with a medium, or grown under conditions which affect one or more cellular process(es) such as the growth, differentiation, or metabolic state of the cell. Thus, if the culture conditions comprise culturing the cell in a medium, the cell is placed in the medium for a sufficient period of time for it to have an effect Likewise, if the conditions are temperature conditions, the cells are cultured at the desired temperature.

The pooling of one or more groups of cell units involves the admixture of the groups to create a single group or pool. In a preferred embodiment, the group or pool comprises cell units of more than one background. For example, said group or pool comprises cell units that have been exposed to more than one different sets of culture conditions. A pool may be subdivided further into groups, either randomly or non-randomly; such groups are not themselves "pools" for the present purposes, but may themselves be pooled by combination, for example after exposure to different sets of culture conditions.

A culture of cells, for example a pool as herein defined, may be split by being subdivided into two or more populations. The subdivision is preferably random, such that cell units are, as far as possible, uniformly divided into different populations. The cell units themselves remain intact. A culture of cells may be split into any number of different populations, limited only by the number of cell units in the starting culture.

Cell growth and cell proliferation are used interchangeably herein to denote multiplication of cell numbers without differentiation into different cell types or lineages. In other words, the terms denote increase of viable cell numbers. In some embodiments, proliferation is not accompanied by appreciable changes in phenotype or genotype.

Embodiments of the invention are described below in detail. Reference is made to the drawings and figures, which illustrate examples of the present invention. Other embodiments, falling within the scope of the appended claims, may depart from the specific details set forth below.

The culture vessel according to the present invention allows cell cultures, including medium and cells, to be repeatedly split and pooled without being withdrawn from the vessel; or split and pooled before being withdrawn from the vessel for incubation between sequential split-pool rounds. It moreover allows for withdrawal and addition of medium and reagents without removing cells. The apparatus may be used to culture cells or cell units, which may comprise cells growing on microcarriers. The culture vessel may be configured in a number of basic shapes, including a flat tray, curved tray and a cylinder. Preferably, the vessel is designed for single use, and is supplied in sterile packaging.

The vessel according to the invention comprises at least two culture compartments and at least one pooling compartment. Cell cultures, including media, cell units and/or cells, can easily be transferred between the culture compartments and the pooling compartment, without the use of external instruments such as pipettes to transfer the cultures. Preferably, the cultures are transferred by rotating or tilting the vessel, to allow the cultures to flow from one area to another.

The number of culture compartments present in each vessel determines the number of "splits" in each split-pool procedure. Preferably, there are between 2 and 10 culture compartments, advantageously 3, 4, 5, 6, 7, 8, 9 or 10 compartments. Larger vessels with greater numbers of compartments can be constructed, for example having up to 15, 20, 50, 75 or 100 culture compartments. In theory there is no limit to the number of culture compartments, but practical considerations include the reduced ease of handling a very large vessel, and difficulties involved in obtaining an effective mixing of cell units if the pooling compartment has to be very large.

Figure 2:
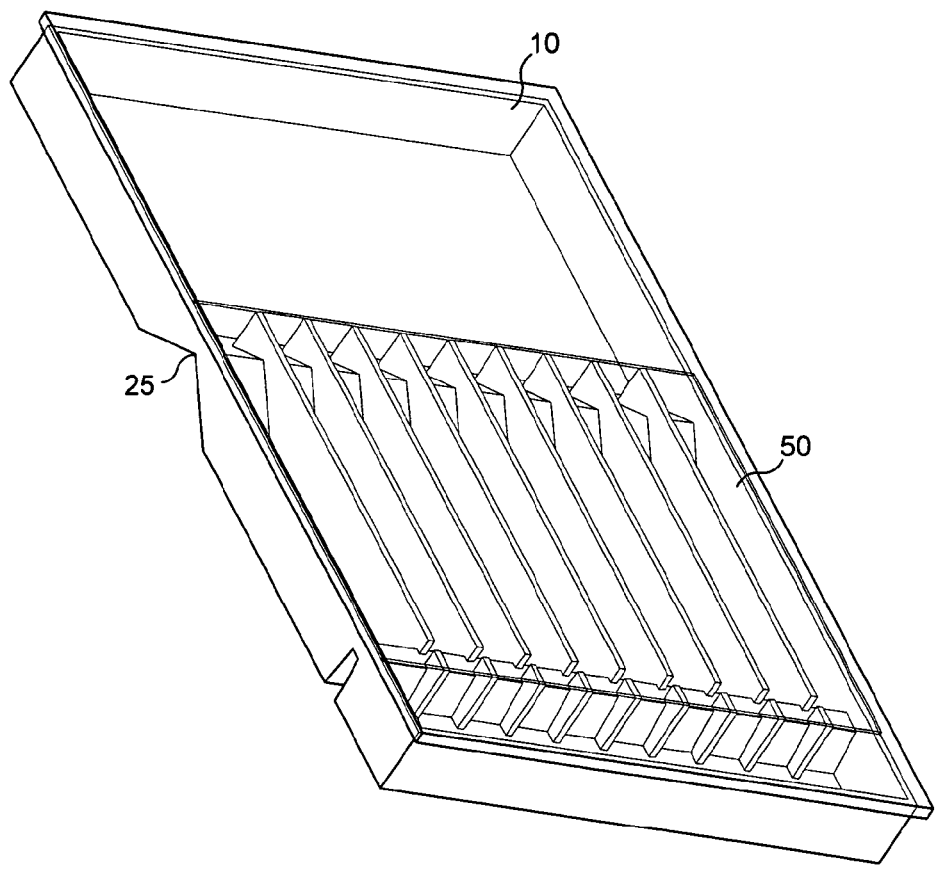
FIG. 2 is another view of the embodiment of FIG. 1.
Figure 3A:
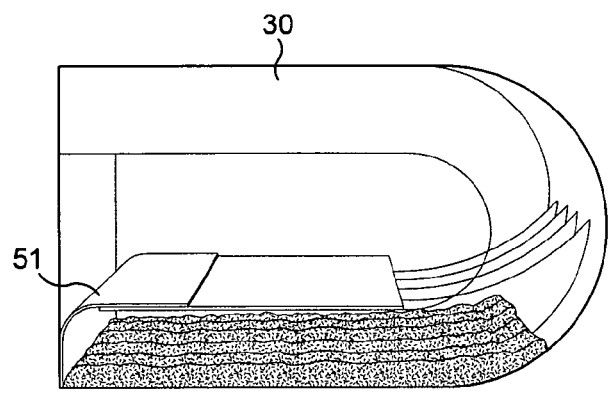
FIG. 3 is a representation of a second embodiment of the vessel of the present invention. Different views are shown in panels A-F.
Figure 3B:
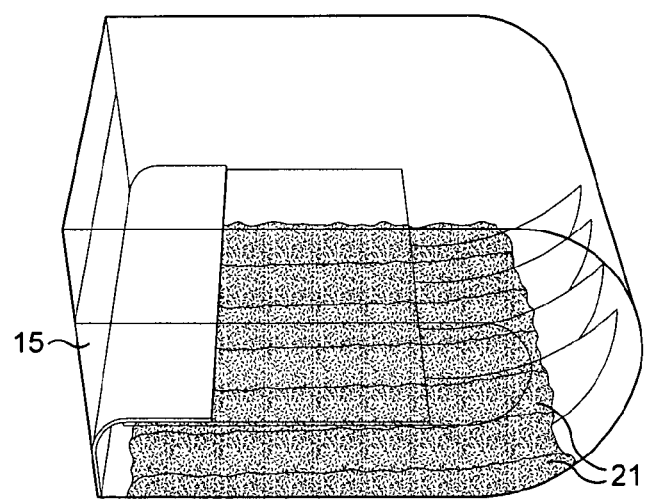
Figure 3C:
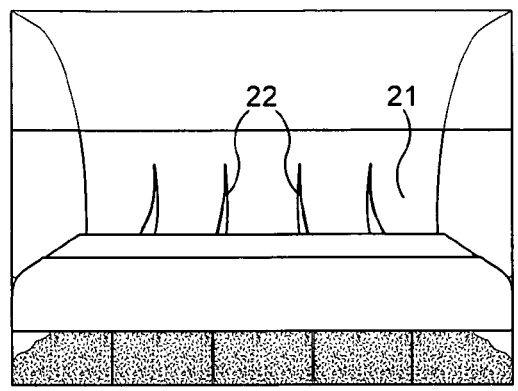
Figure 3D:
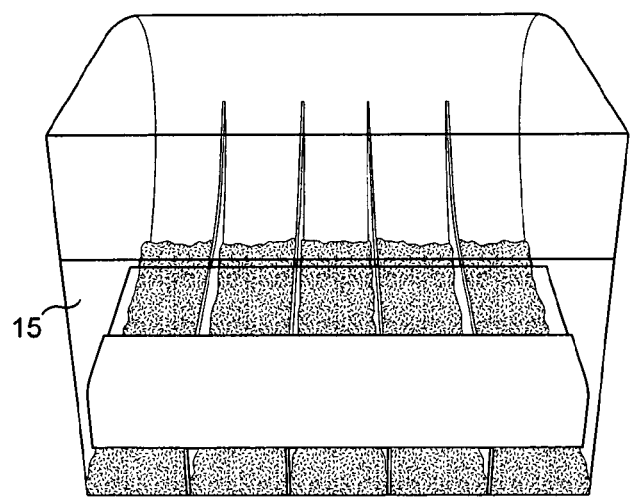
Figure 3E:
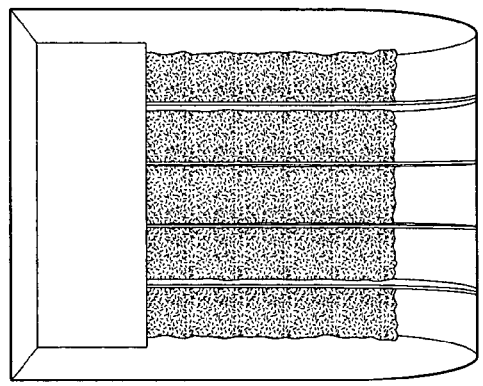
Figure 3F:
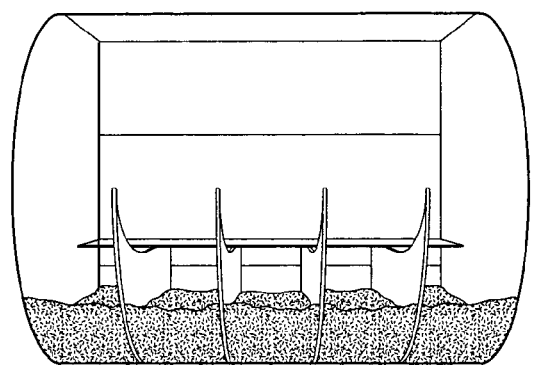
Figure 4A:
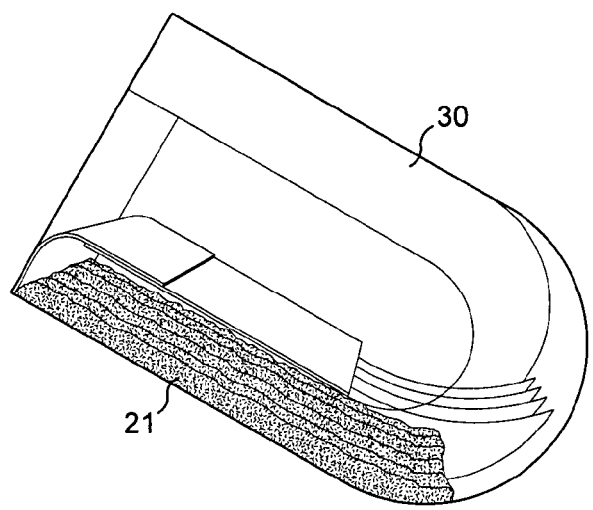
FIG. 4 illustrates the operation of the pooling compartment of the embodiment of FIG. 3.
Figure 4B:
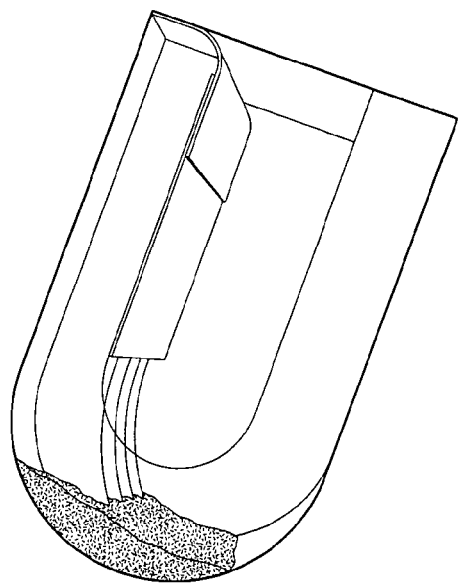
Figure 4C:
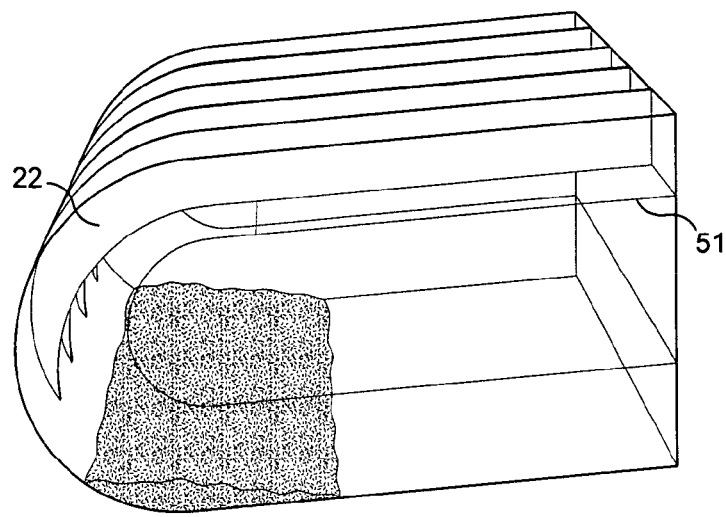
Figure 4D:
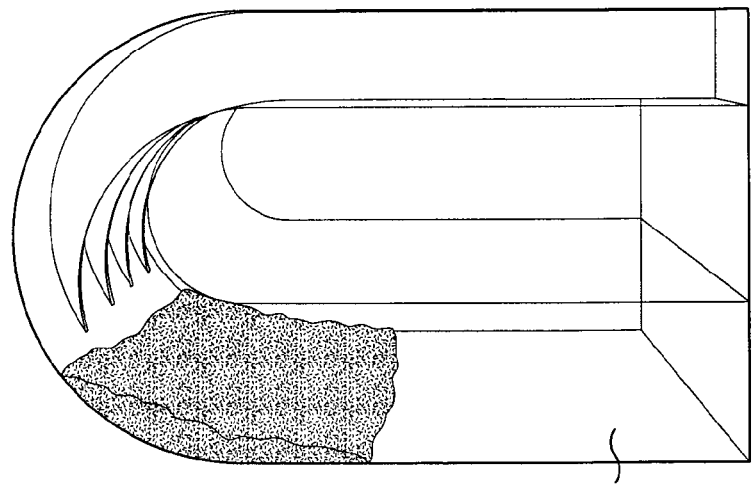
Figure 4E:
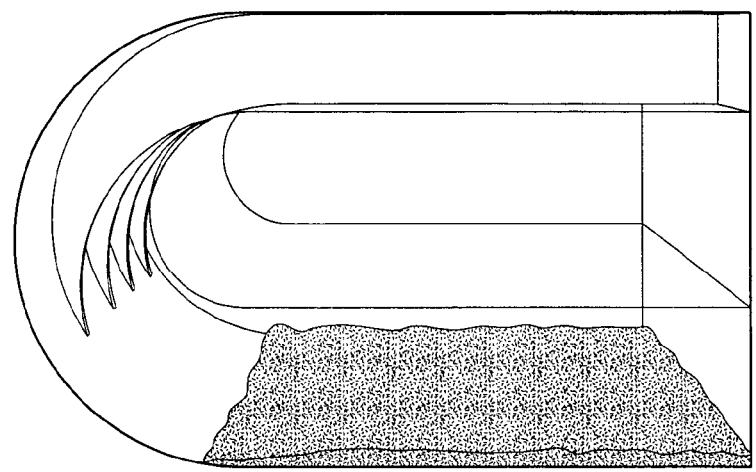
Figure 4F:
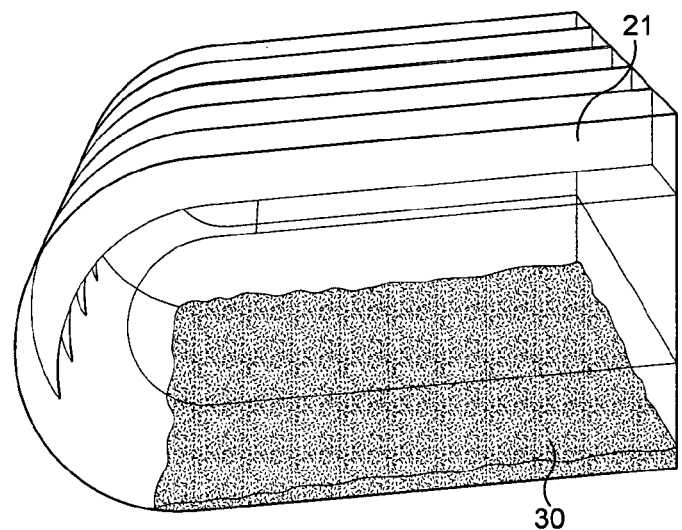

Considering a first embodiment shown in FIG. 1, culture vessel 10 is in the form of a simple tray design. The vessel comprises parallel culture compartments 21, separated by walls 22. Pooling compartment 30 is positioned at one end of the channel-shaped culture compartments. Divider 25 separates the pooling compartment from the culture compartments. In use, cell cultures present in culture compartments 21 can be transferred to pooling compartment 30 by tilting the vessel, thus allowing the cell cultures to pass over divider 25. Divider 25 is optional, since the cell cultures may be retained in the culture compartments or the pooling compartment by adjusting the tilt of the vessel. As shown in FIG. 2, a lid 50 may be present, to prevent contamination of the cultures by foreign elements and by spillage between the culture compartments. Seals between lid 50 and walls 22 allow the vessel to be angled more steeply, for improved transfer of cell cultures between the culture and pooling compartments without spillage of cell cultures. It also allows greater angles of tilting to retain the cultures in the culture compartments if divider 25 is absent. It also allows complete tilting of the device to drain media when using a filter, which is located at the end of each culture compartment.

Pooling compartment 30 may comprise walls of increased height, better to contain the cell cultures when they are transferred from the culture compartment. A cover, sealing the pooling compartment, may also be provided.

Figure 9:
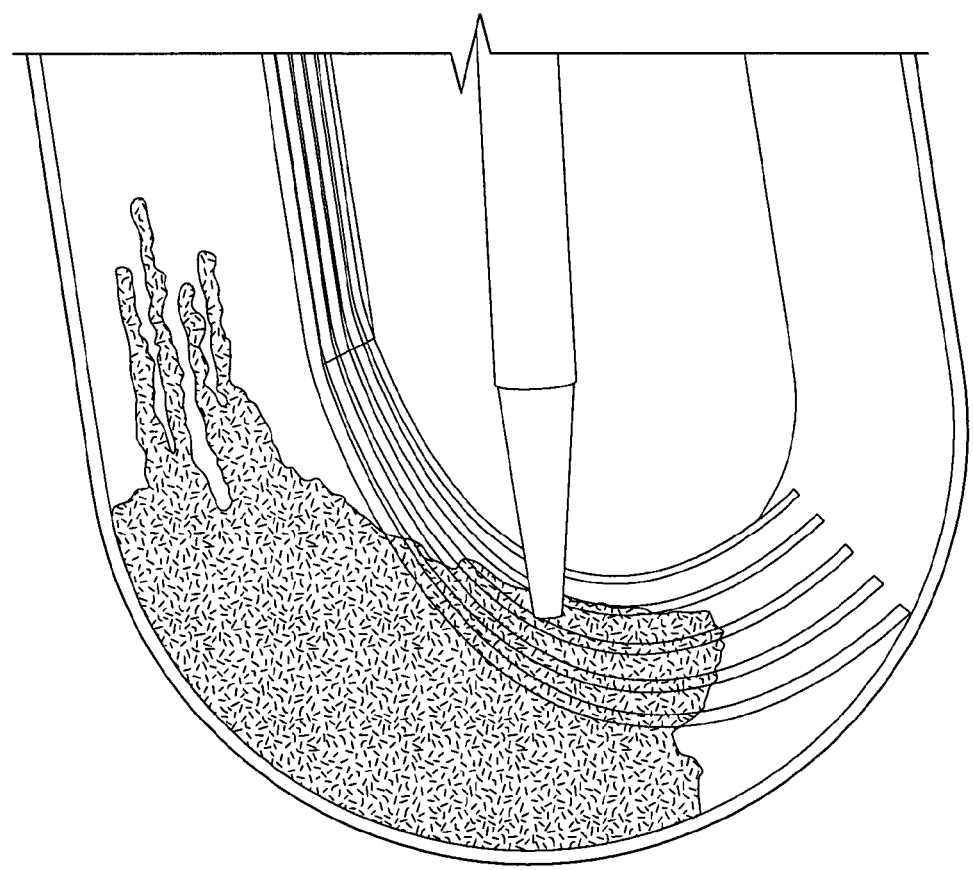
FIG. 9 illustrates an embodiment of the vessel in which one or more or each of the dividers between the channels are extended into the curved region of the vessel.

FIG. 3 shows a second embodiment, which is in the form of a curved tray. Culture compartments 21 are in the form of channels, separated by walls 22 and covered by a cover 51. The bottom of the vessel, and the walls 22, extend arcuately upwards at one end of the vessel, such that compartments are still present at the curved bottom of the vessel but a pooling compartment 30 exists in an inverted position above the culture compartments. When the vessel is tilted, the cell cultures remain segregated in the channel-like culture compartments present in the curved region at the end of the vessel. The vessel can be tilted further until it is inverted, such that the cell cultures are transferred to the pooling compartment 30. Opening 15 allows access to the compartments 21 and 30. In one embodiment, the dividers between the channels are extended into the curved region at the end of the vessel, to keep the cultures segregated in the curved region, as shown in FIG. 9. A pipette can then be placed vertically into each compartment from the opening 15 directly above, e.g. by a robot.

FIG. 4 shows the process of inversion of the vessel, and mixing of the cell cultures in the pooling compartment. In step A, the vessel is tilted onto its arcuate surface, such that by step B the cell cultures have flowed from the culture compartments into the space formed by the curvature of the vessel bottom, and are no longer separated by walls 22. steps C and D show further tilting of the vessel, such that the cell cultures come to rest in pooling compartment 30, and are now combined. The vessel may be subjected to shaking, leading to a single, combined culture of cells as shown in steps E and F.

Figure 5A:
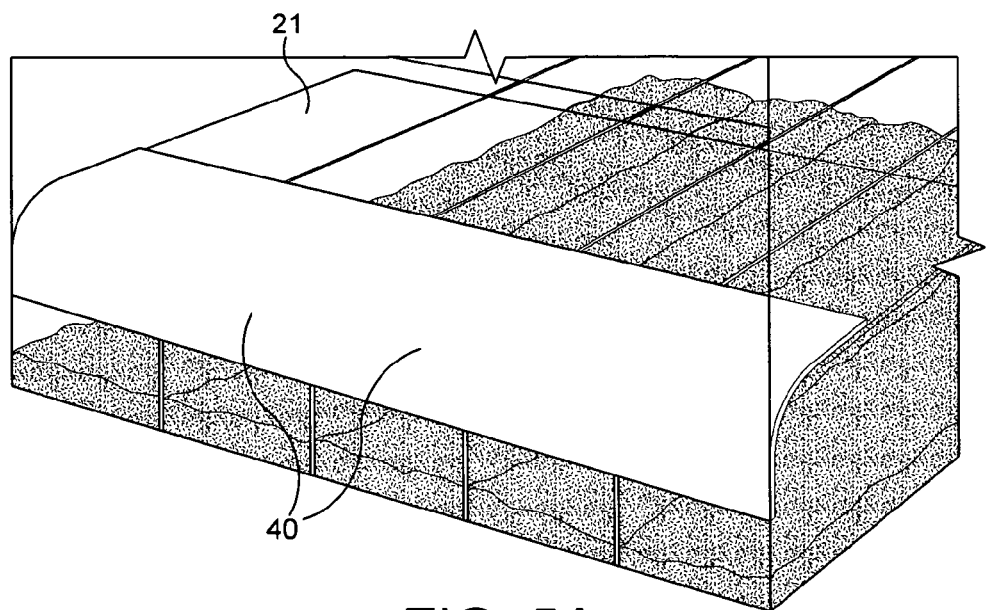
FIG. 5 illustrates the operation of the ports in the culture compartments of the embodiment of FIG. 3, allowing draining of medium therefrom.
Figure 5B:
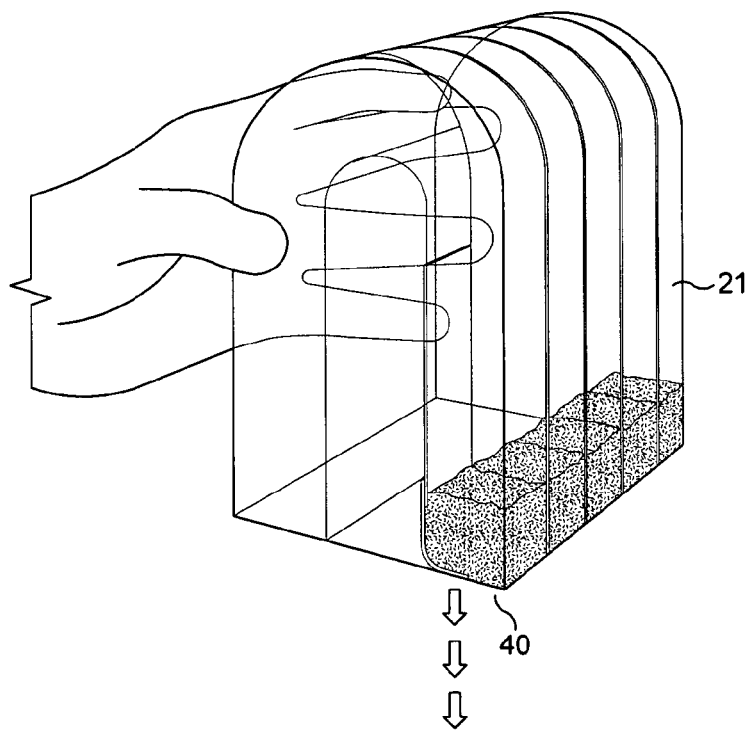

FIG. 5 shows the filter-covered ports 40, and inversion of the culture vessel to drain medium from the culture compartments 21 (FIG. 5*b*). Ports 40 are provided with filters which allow the removal of medium from the culture compartments whilst retaining the cells or microcarriers therein. The filter advantageously allows <20 micron tags to pass, but retain >100 micron microcarriers. It is preferably non-stick, such as not to retain any tags, cells or microcarriers attached thereto. For example, a 70 micron nylon mesh may be used.

Figure 6:
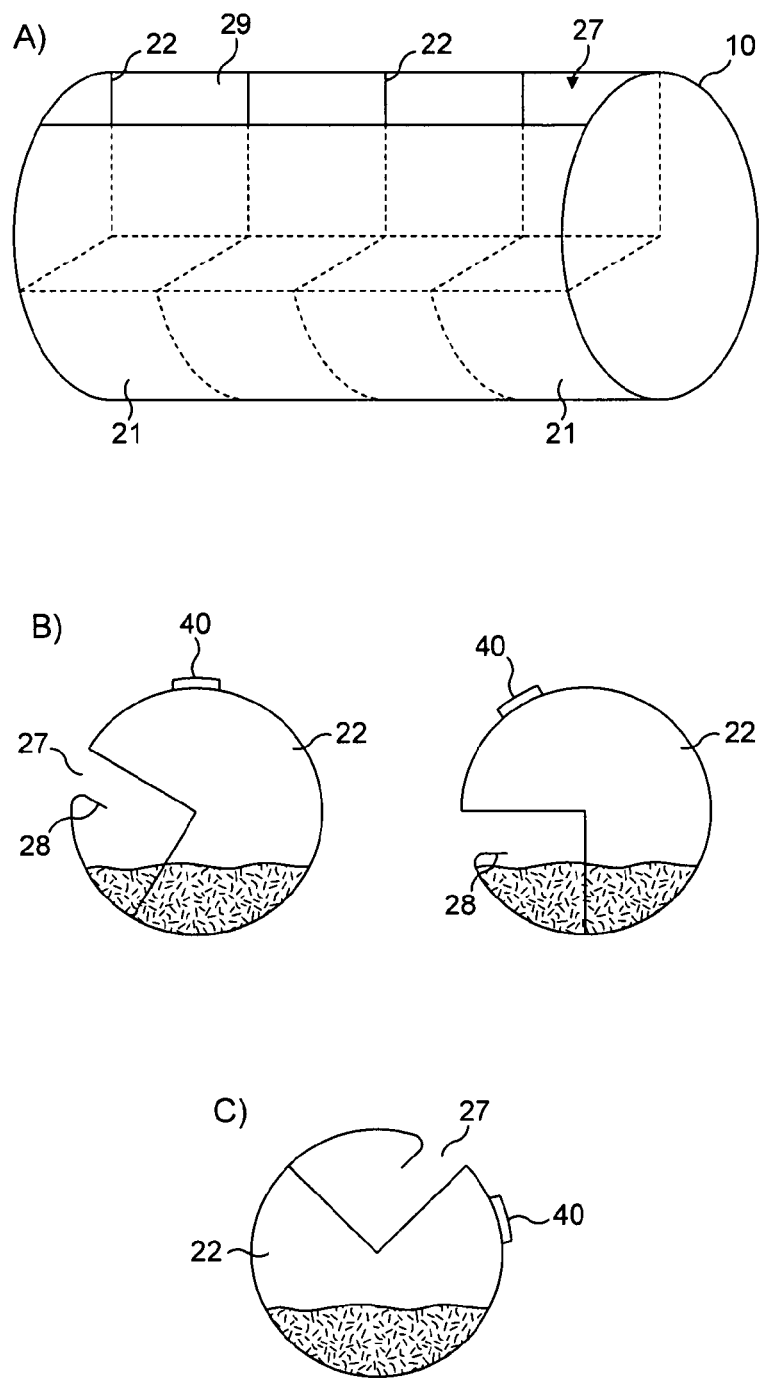
FIG. 6 illustrates a third embodiment of the present invention.

A third embodiment is shown in FIG. 6. In this embodiment, the vessel is a cylindrical bottle 10 subdivided by radial walls 22 to form culture compartments 21. Radial walls 22 do not extend around the entire circumference of cylinder 10, thus forming a pooling compartment 30 which extends along the length of the cylinder 10. As shown in FIG. 6*b*, rotating the cylinder about its longitudinal axis allows the cell cultures present in culture compartments 21 to flow into the pooling compartment 30, where they are no longer separated by walls 22 and are therefore mixed. Ports 40 are located diametrically substantially opposite the pooling compartment. Rotation of the cylinder in the direction of ports 40 (FIG. 6*c*) will allow the media to be drained from the culture compartments. The cell cultures remain separated by walls 22. Walls 22 are faced with a sealing plate 29, which is substantially vertical as shown in FIG. 6*a*. This plate helps prevent cross-contamination of cultures when media are drained through ports 40. Cylinder 10 comprises a slot 27 running along its length, which allows access to the culture compartments. Optional lip 28 helps to prevent spillage when the cultures are transferred to the pooling compartment.

Figure 7:
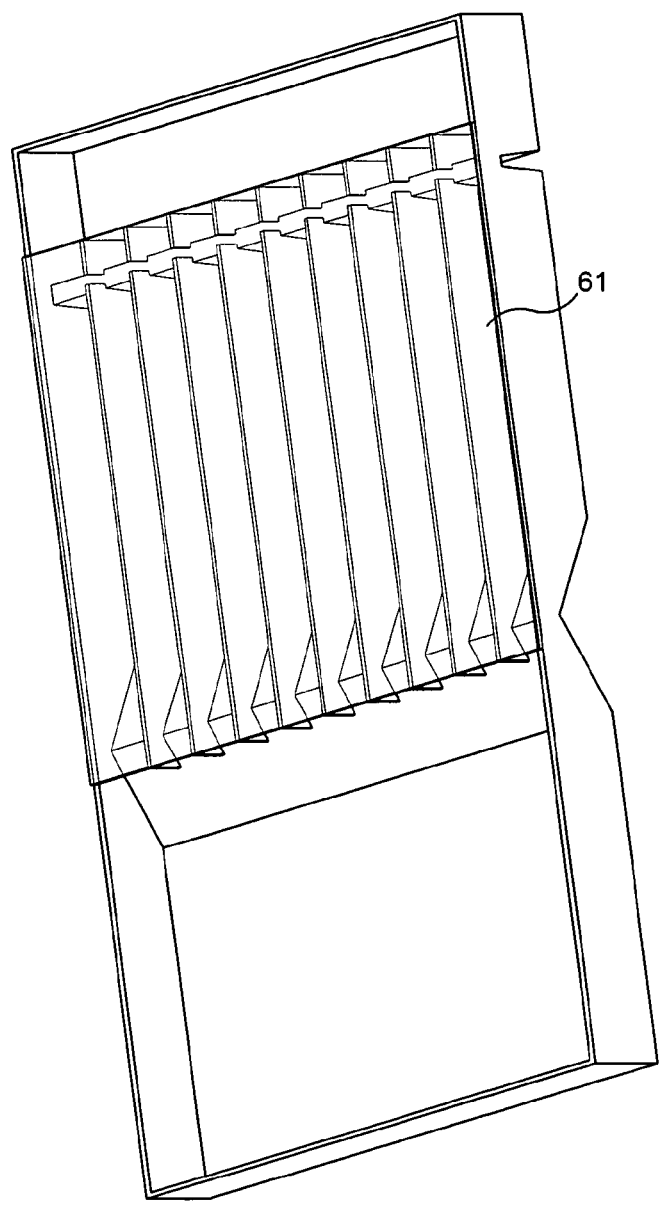
FIG. 7 illustrates the vessel comprising a cover over the whole device
Figure 8:
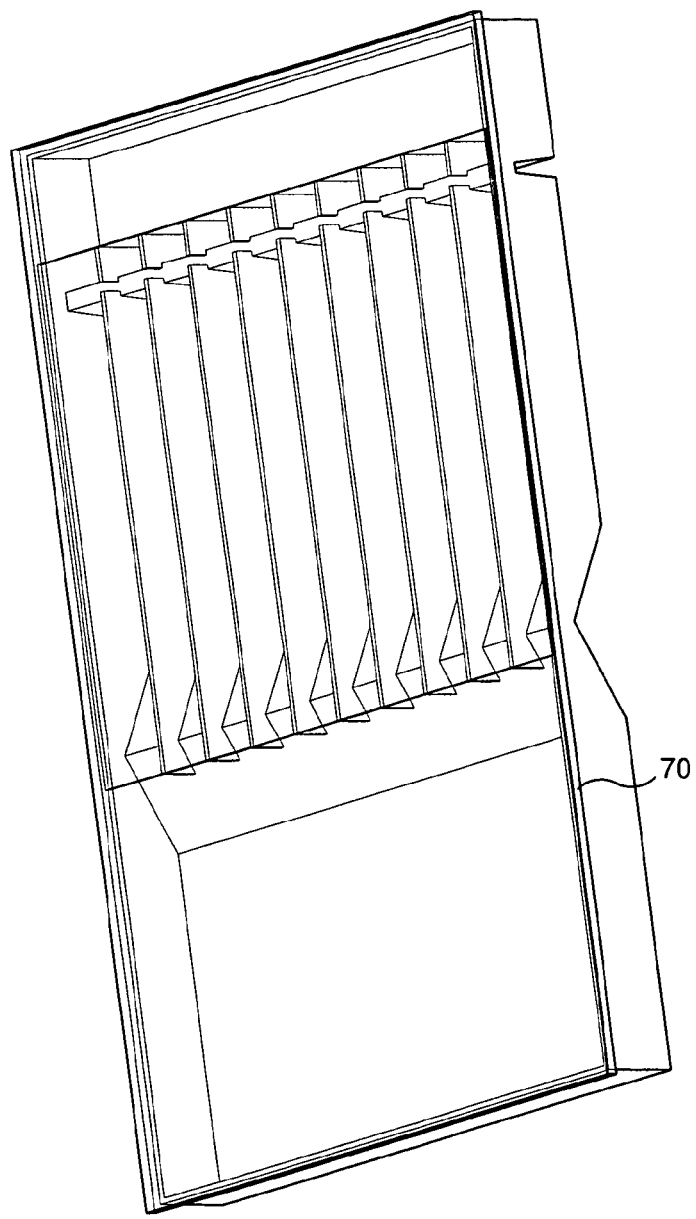
FIG. 8 illustrates the vessel comprising a sealed lid to cover the divided compartments.

Further embodiments of the culture vessel are shown in FIGS. 7 and 8. As shown in FIG. 7, the vessel comprises a cover 61 over the whole device to prevent contamination. In FIG. 8, the vessel comprises sealed lid 70 which covers the divided compartments to prevent contamination between the compartments.

A modified culture vessel 100 is illustrated in FIGS. 10 to 16. The modified culture vessel 100 is based closely on the second embodiment and like reference numerals have been used for like components albeit incremented by 100 for the sake of clarity. The use of the culture vessel 100 is the same as that described herein for the second embodiment.

Figure 10:
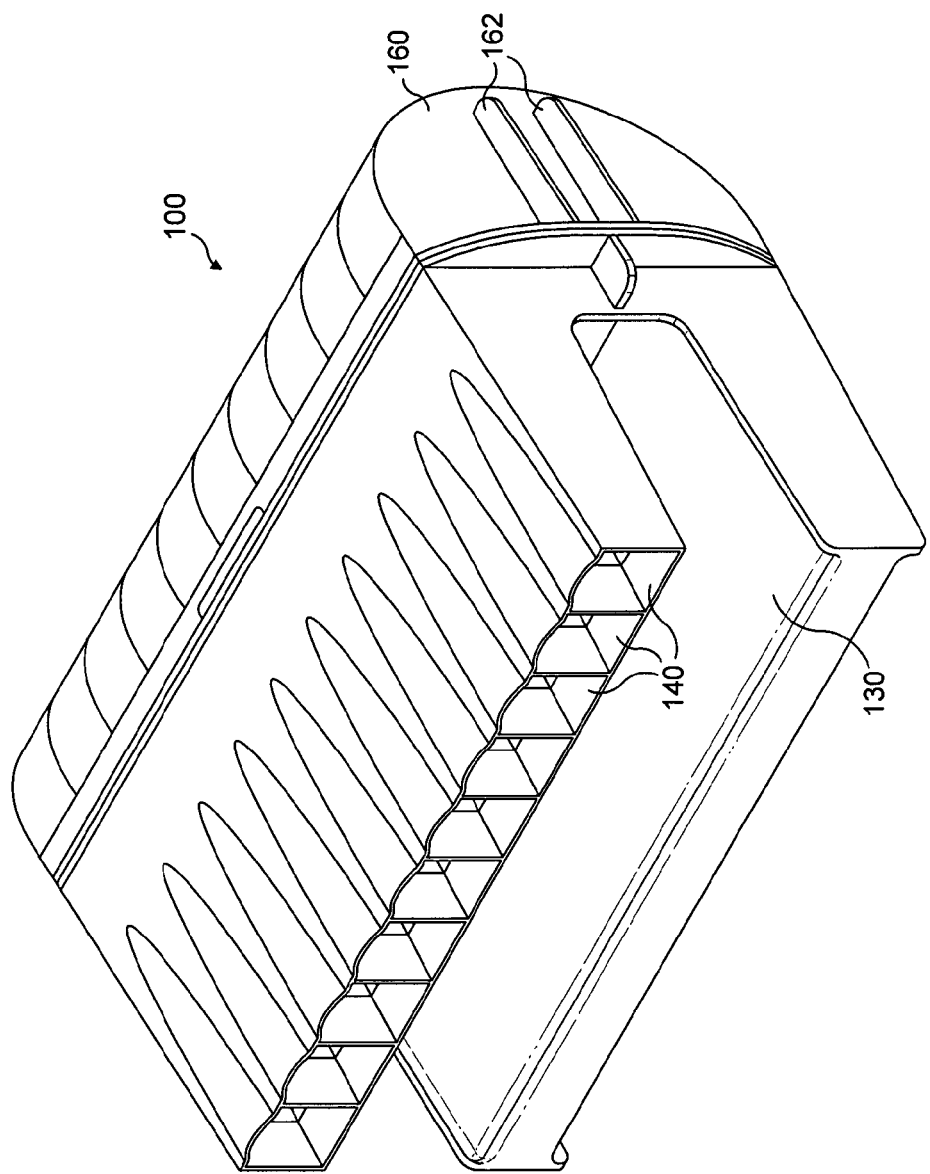
FIG. 10 illustrates a perspective view of a refined version of the apparatus according to the second embodiment of the present invention.
Figure 11:
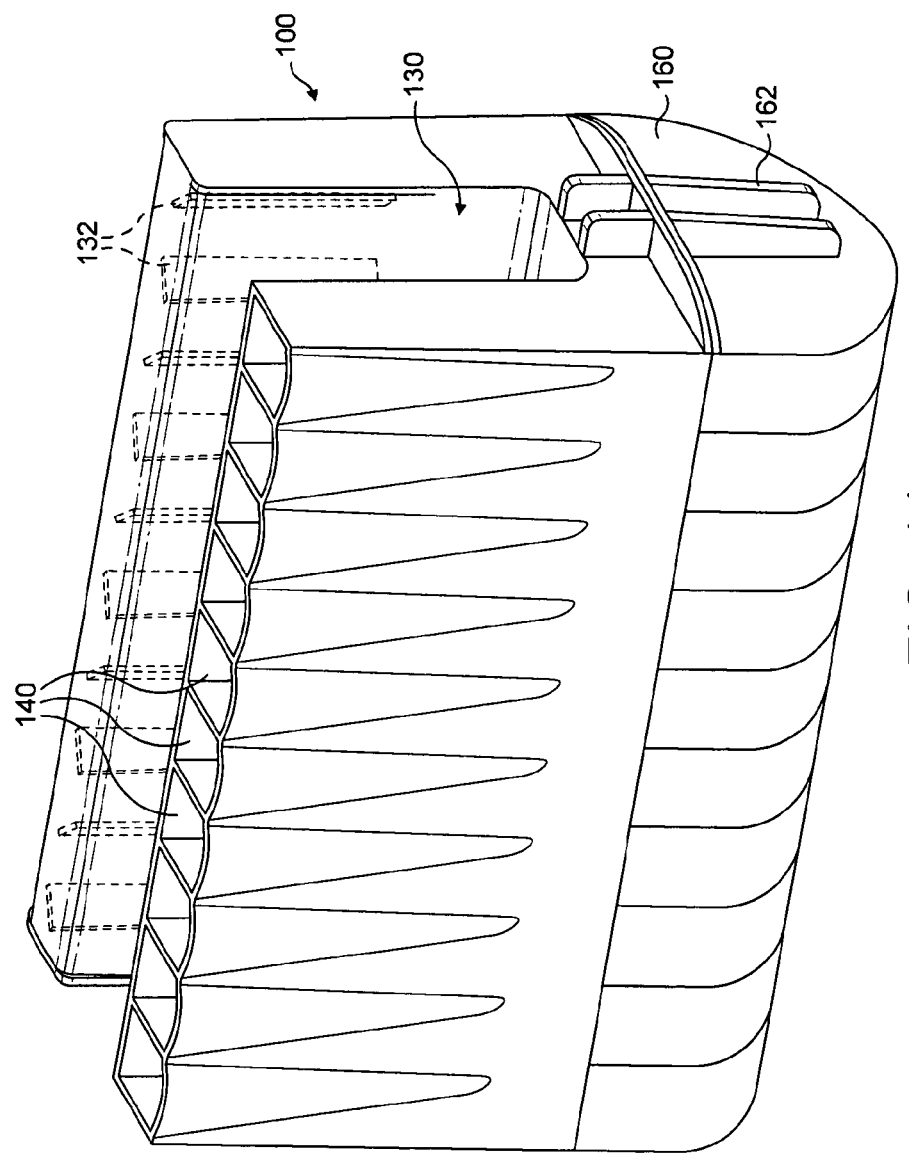
FIG. 11 illustrates a perspective view of the apparatus of FIG. 10 in a transparent form to show the internal structure thereof.

The culture vessel 100 comprises first and second arms arranged in a U-shape. An array of filter-covered ports 140 is formed in the first arm of the vessel 100 and a pooling compartment 130 is formed the second arm. The first and second arms are joined by an intermediate section defining a plurality of culture compartments 121 separated by internal walls 122. The ports 140 each have a filter over their open ends to allow media to be drained. A perspective view of the culture vessel 100 is illustrated in FIG. 10 and the internal structure is illustrated in the partially transparent view of FIG. 11. As shown in FIG. 11, mixing fins 132 are provided in the pooling compartment 130 to promote mixing.

The culture vessel 100 has first and second end walls 160. Volume levels are marked on both end walls to indicate the maximum volume of the separate culture compartments. At least one mounting member 162 is formed on each end wall 160 to enable the culture vessel 100 to be supported in a stand 200 (described below with reference to FIGS. 17 to 20). In the present embodiment, the mounting members 162 are asymmetric so that the culture vessel 100 can only be located in the stand 200 in a predetermined orientation (for example to position the ports 140 towards the front or towards the back of the stand 200). Specifically, two substantially parallel mounting members 162 are formed on the first end wall 160 and one mounting member 162 is formed on the second end wall 160 to provide the desired asymmetric (or handed) configuration of the culture vessel 100. It will be appreciated that alternative configurations of the mounting members 162 can be employed to provide the desired asymmetric arrangement. However, it is not essential that the culture vessel 100 is asymmetric and a symmetrical configuration may be employed for the mounting members 162.

Figure 12:
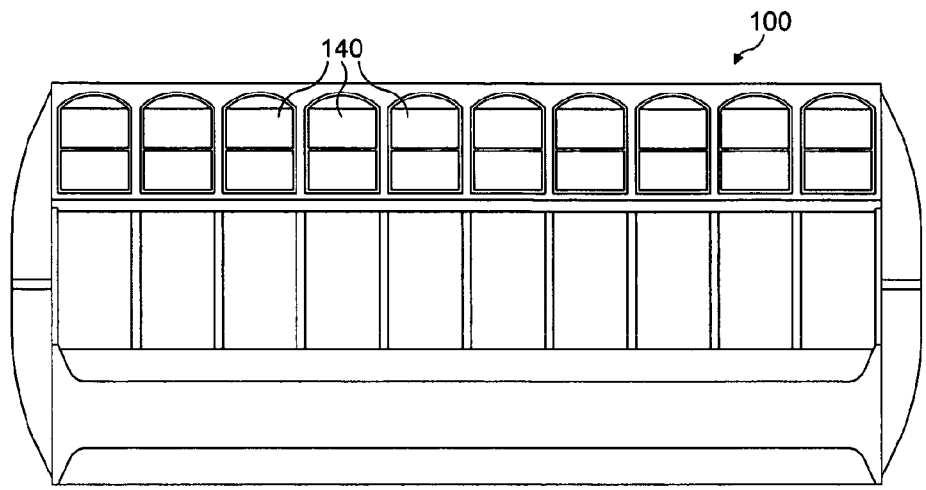
FIG. 12 illustrates a plan view of the apparatus of FIG. 10.
Figure 13:
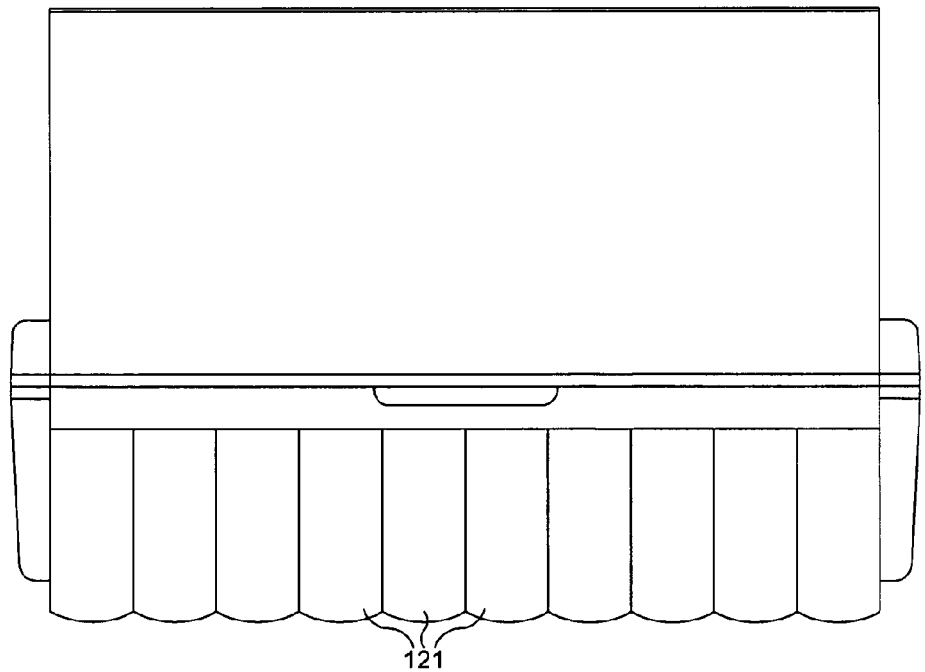
FIG. 13 illustrates a side view of the apparatus of FIG. 10.
Figure 14:
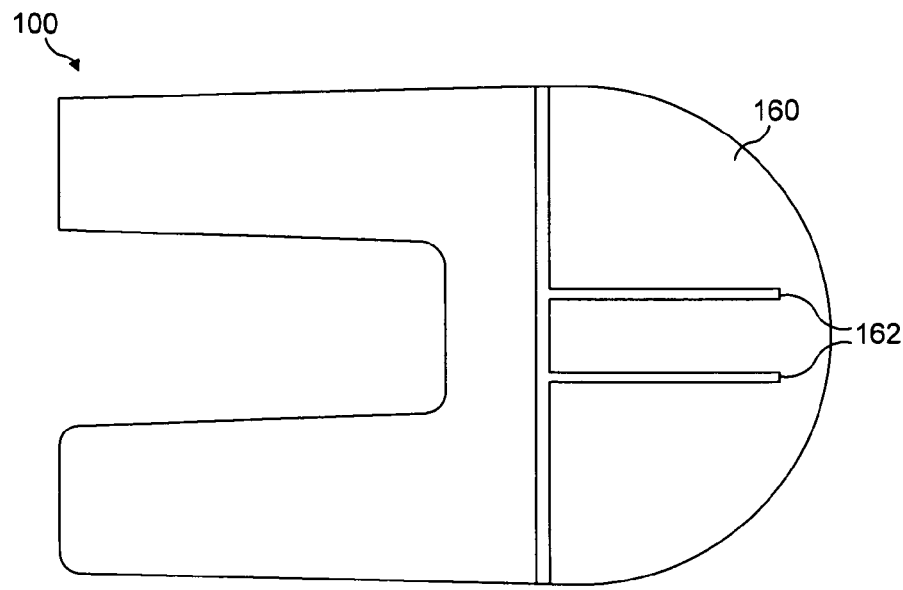
FIG. 14 illustrates an end view of the apparatus of FIG. 10.
Figure 15:
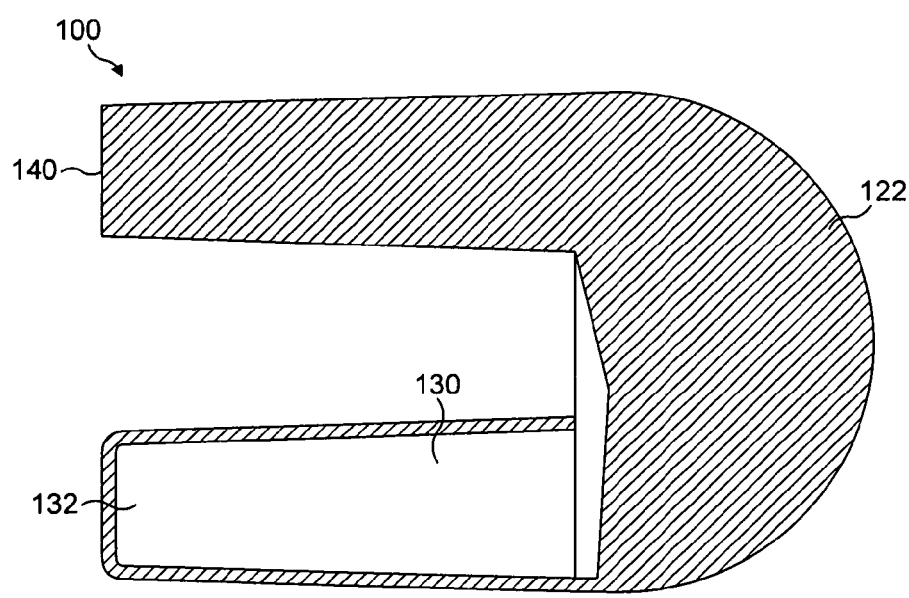
FIG. 15 illustrates a cross-sectional view of the apparatus along the line H-H of FIG. 10.

As shown in the respective plan and side elevations of FIGS. 12 and 13, the culture compartments 121 have a convex external profile allowing better removal of cell cultures. An end view of the culture vessel is shown in FIG. 14. As mentioned above, a series of elongate mixing fins 132 are provided along the length of the pooling compartment 130. The mixing fins 132 are shown most clearly in the cross-sectional view of FIG. 15.

Figure 16A:
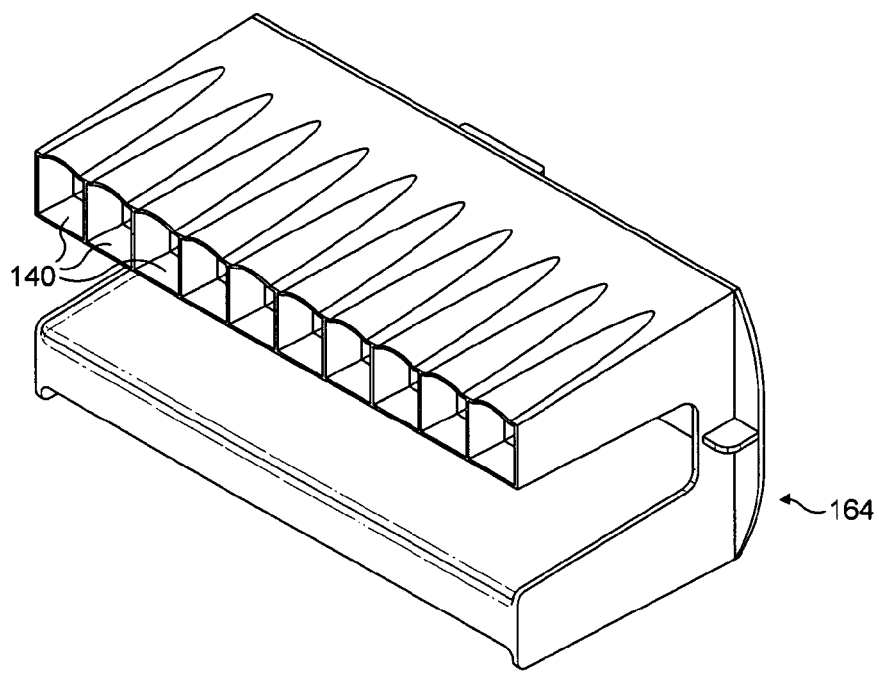
FIGS. 16A, 16B and 16C illustrate perspective views of the separate components for forming the apparatus of FIG. 10.
Figure 16B:
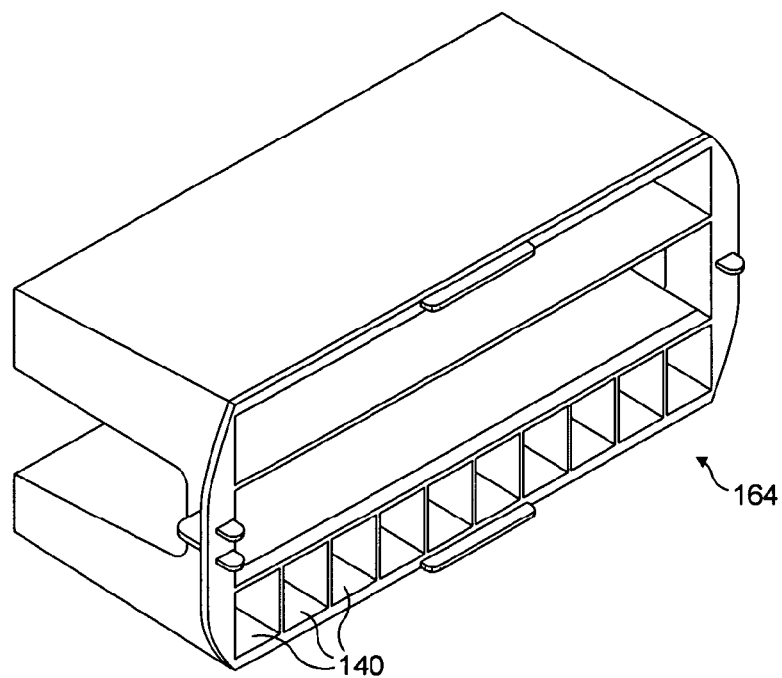
Figure 16C:
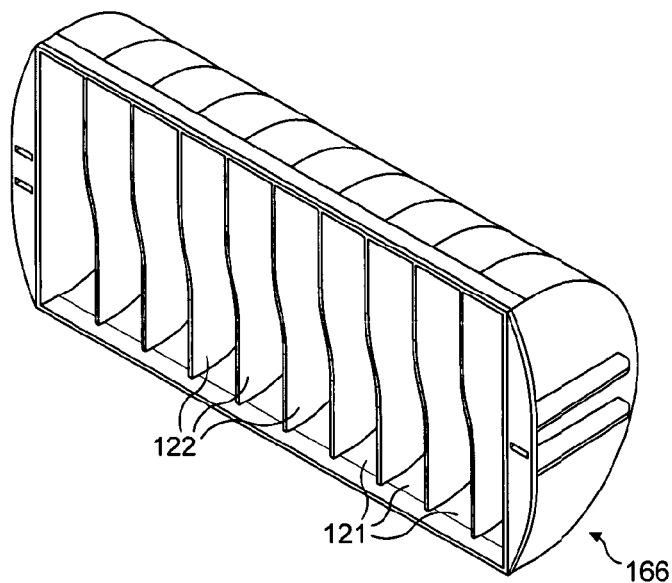

The culture vessel 100 is made up of a first component 164 (shown in FIGS. 16A and 16B) and a second component 166 (shown in FIG. 16C). The first component 164 defines the ports 140 and the pooling compartment 130. The second component 166 defines the compartments 121 and the plurality of intermediate walls 122 which separate them. The first and second components 164, 166 are injection moulded separately and then joined together. When assembled, the compartments 121 formed in the second component 166 define pathways between the first and second arms of the culture vessel 100.

Figure 17:
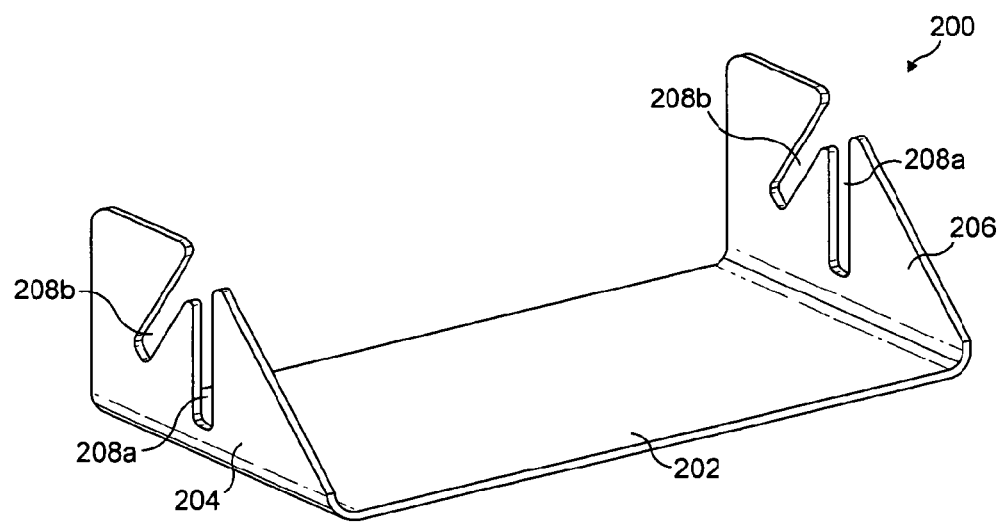
FIG. 17 illustrates a perspective view of a stand for the apparatus.

The present application also relates to a stand 200 for the culture vessel 100. As shown in FIG. 17, the stand 200 comprises a base 202 and first and second frame members 204, 206. The stand 200 is made of a material that can be sterilized, e.g. with 70% ethanol solution. It is envisaged that the stand 200 could be made of stainless steel or a plastics material such as polycarbonate, polystyrene or Teflon. The frame members 204, 206 each have first and second matching slots 208a, 208b in which the mounting members 162 locate. The slots 208a, 208b in each frame member 204, 206 are angularly offset from each other. In the present embodiment, the first slots 208a are operatively arranged vertically and the second slots 208b are operatively inclined at an angle of 45° to the vertical. It is envisaged that the slots 208a, 208b could be arranged at different angles. Moreover, the frame members 204, 206 could each have only a single slot 208 or could each have more than two slots 208.

Figure 18A:
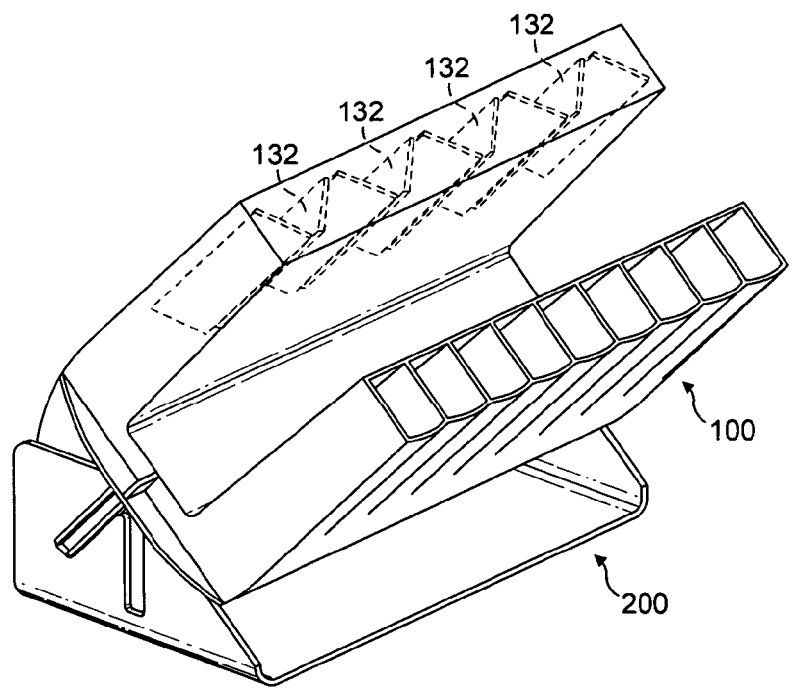
FIGS. 18A and 18B illustrates the apparatus in first and second different positions in the stand of FIG. 17.
Figure 18B:
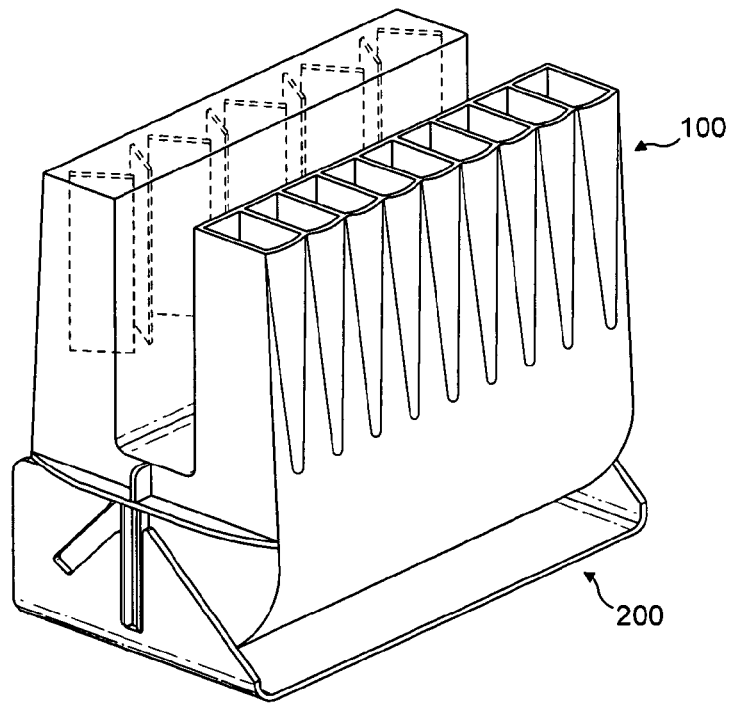
Figure 19A:
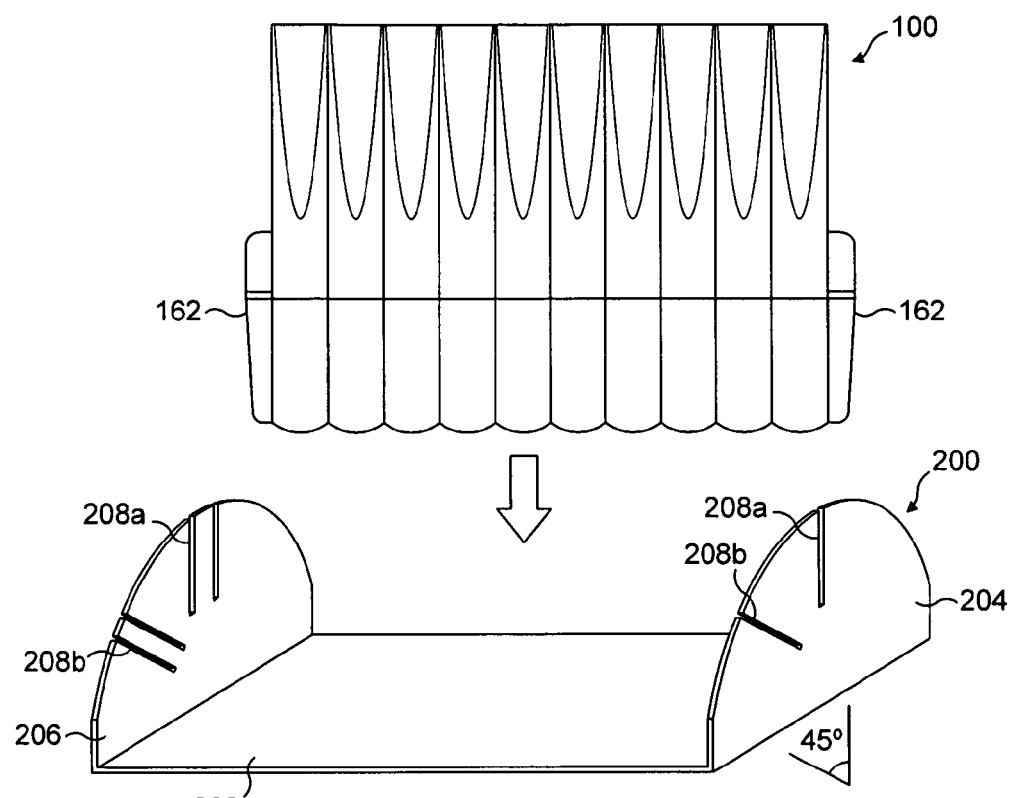
FIGS. 19A and 19B illustrate schematically the use of the stand to position the apparatus in the first position.
Figure 19B:
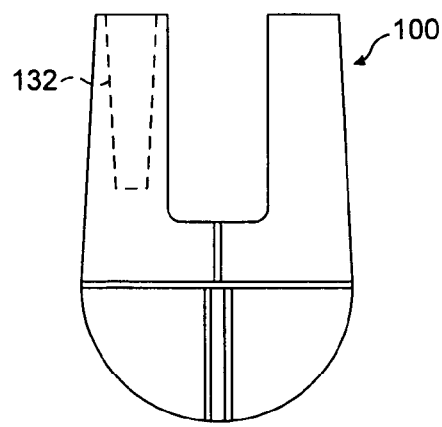

The culture vessel 100 according to the present invention is shown positioned in the stand 200 in an inclined position in FIG. 18A. The culture vessel 100 is shown positioned in the stand 200 in a vertical position in FIG. 18B. The positioning of the culture vessel 100 in the stand 200 in a vertical position is illustrated schematically in FIGS. 19A and 19B. The stand 200 can be provided with asymmetric slots 208a, 208b for cooperating with the asymmetric fins 162 provided in the culture vessel 100, as illustrated in FIG. 19A.

Figure 20A:
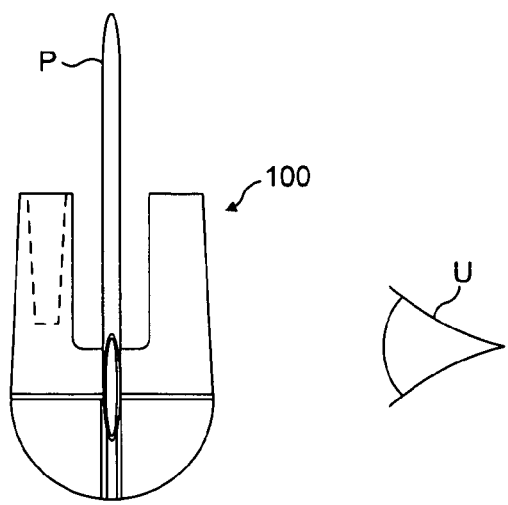
FIGS. 20A and 20B illustrate schematically the use of the stand to position the apparatus in first and second different positions.
Figure 20B:
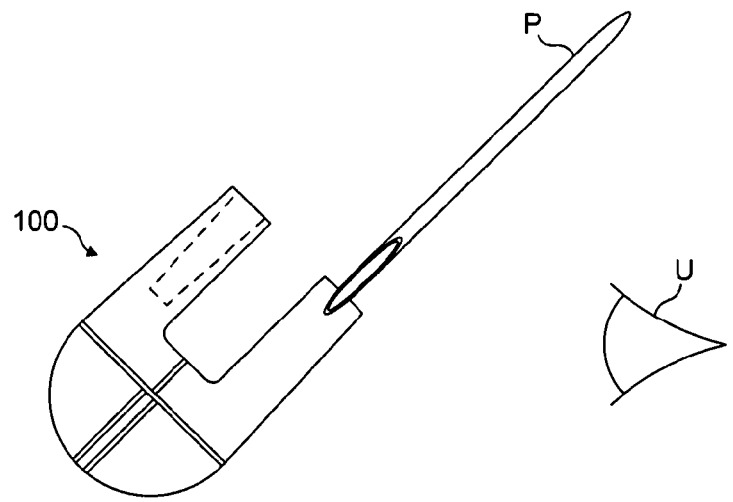

The different vantage points provided for a user U with the culture vessel 100 located in respective vertical and inclined position are illustrated in FIGS. 20A and 20B respectively. The different positions also alter the access to the interior of the culture vessel 100 and access to the ports and filter 140, for example with a pipette P.

It will be appreciated that the culture vessel according to the present invention can be operated in two modes, namely:

i) performing the split, pool and incubation rounds in the culture vessel; and ii) performing pooling and splitting rounds in the culture vessel before removing the cell culture for incubation in a separate container. In the second operational mode, the cell culture can be removed in isolation from the separate compartments or collectively from the pooling compartment. The culture vessel 100 is particularly well suited for use according to the second of these modes in which the split bead suspensions are removed for incubation in a different container.

The culture vessel of the present invention is useful for exposing cells to multiple tissue culture conditions. Preferably, the cells are grouped into cell units. Each cell unit constitutes an easily handled unit that can be exposed to a variety of cell culture conditions. In accordance with the present invention, cell groupings are typically produced by growing cells in microcarrier culture, and the terms cell unit, cell group, colony and bead are used interchangeably. A particularly efficient method for sampling a large number of cell culture conditions is referred to as Combinatorial Cell Culture or split-pool cell culture and in one embodiment involves the serial subdividing and combining of groups of cell units in order to sample multiple combinations of cell culture conditions.

In one aspect of the invention the method operates by taking an initial starter culture (or different starter cultures) of cell units and dividing it into a number of aliquots by separating it into the culture compartments of the culture vessel. Each compartment contains multiple units (beads/groups/colonies/carriers). The units in each compartment are subjected to different culture conditions. Following cell culture for a given time, the cell units can be pooled by transferring the cell units to the pooling compartment. This pool can be split again into the culture compartments, each of which is subjected to different conditions for a period of time, and subsequently also pooled. This iterative procedure of splitting, culturing and pooling cell units (or pooling, splitting and culturing; depending on where one enters the cycle) allows systematic sampling of many different combinations of cell culture conditions. The complexity of the experiment, or in other words the number of different combinations of cell culture conditions tested, is equal to the product of the number of different conditions sampled at each round. Note that the step of pooling all the cell units prior to a subsequent split can be optional; a step in which a limited number of cell units are pooled can have the same effect. The invention therefore facilitates a number of related methods of systematically sampling multiple combinations of cell culture conditions where groups of cell units are handled in bulk.

Regardless of the precise manner in which a diversity of cell culture conditions is sampled by this means the procedure is efficient because multiple cell units can share a single vessel, where they may be cultured (eg. under different conditions) or transferred. The number of split samples which can be generated depends on the number of culture compartments included in the vessel.

In many respects the principle of this procedure resembles that of split synthesis of large chemical libraries (known as combinatorial chemistry), which samples all possible combinations of linkage between chemical building block groups (see for example: Combinatorial Chemistry, Oxford University Press (2000), Hicham Fenniri (Editor)).

Split-pool cell culture can be repeated over any number of rounds. More than one vessel may be used simultaneously, meaning that any number of conditions can be sampled at each round.

This procedure can be used to sample growth or differentiation conditions for any cell type, or the efficiency of biomolecule production (e.g. production of erythropoietin or interferon) by any cell type. Because the procedure is iterative, it is ideally suited to testing multistep tissue culture protocols—for instance those described above in connection with stem cell differentiation. The variables which can be sampled using this technique include cell type, cell grouping (e.g. microcarrier culture, cell encapsulation, whole organism), growth substrate (e.g. fibronectin on microcarrier), different culture media (including different concentrations of constituents), growth factors, conditioned media, co-culture with various cell types (e.g. feeder cells), animal or plant extracts, drugs, other synthetic chemicals, infection with viruses (incl. transgenic viruses), addition of transgenes, addition of antisense or anti-gene molecules (e.g. RNAi, triple helix), sensory inputs (in the case of organisms), electrical, light, temperature, oxygen partial pressure, carbon dioxide, partial pressure and/or red-ox stimuli and others.

In an example of a split-pool procedure carried out using the vessel as shown in FIG. 3, in step 1 microcarriers carrying cells can be transferred by pipetting from one or more culture plate, either into the individual channels 21, or into pooling compartment 30, through opening 15. If the microcarriers are added to pooling compartment 30, the vessel is inverted to transfer the culture to culture compartments 21.

In step 2, the vessel is placed in the position shown in FIG. 5b, to remove any growth media and tags.

In step 3, microcarriers stuck to the filters on ports 40 are removed by backwashing with 5 ml of a wash buffer.

In step 4, the culture compartments are filled with 13 ml wash buffer, and the contents mixed.

In step 5, the wash buffer is drained off, as per step 2. Steps 3 to 5 may be repeated three times, to remove any excess tags and previous culture medium components.

In step 6, pooling medium is added and the microcarriers are pooled by tilting the vessel, as shown in FIG. 4.

In step 7, the microcarriers are split between each of the culture compartments by reversing the procedure shown in FIG. 4.

In step 8, the pooling medium is removed by placing the vessel in the position shown in FIG. 5b.

In step 9, any microcarriers adhering to the filter are washed off using the medium to which it is intended to expose the cells.

In step 10, the culture compartments are filled with the desired medium. Further reagents may be added at this time, as required.

In step 11, cells may be cultured in situ in the culture compartments, or transferred from the culture compartments to a new culture plate for incubation.

Selected tags and cell culture reagents can now be added, to vary the conditions within each culture compartment, and the cells are cultured.

More complex split-pool combinations can be provided by using a means for bulk transfer of cell cultures, such as manual or automated pipettes, to transfer cell cultures from a culture compartment to another vessel, which may be a vessel in accordance with the present invention, or may be a conventional vessel such as a culture plate. For example, a cell culture can be transferred to the pooling compartment of a vessel according to the invention, and repeatedly split and pooled, exposing the cell units to a number of culture conditions. Units from each individual culture compartment, after the final splitting, can then be transferred to another vessel and optionally combined with cell units from a separate experiment. These units can then be further split, and subjected to different culture conditions.

If necessary culture vessels of different sizes, accepting different volumes of cell culture, may be used. For example, when the contents of a single culture compartment are to be split, a smaller vessel may be used. Conversely, if the entire contents of two or more vessels are to be pooled, a larger vessel may be used.

Kits according to the invention may be supplied with microcarriers. A variety of microcarriers are available, ranging in shape and size and made of different materials. Microcarriers may be porous, macroporous, microporous or solid. By way of example, the microcarrier may be a microcarrier selected from the group consisting of a Cultispher microcarrier, a Cultispher-G microcarrier, a Cultispher-GL microcarrier, a Cultispher-S microcarrier, an Informatrix microcarrier, a Microsphere microcarrier, a Siran microcarrier, a FibraCel® Disks microcarrier, a Cytoline microcarrier (e.g. a Cytoline 1 microcarrier or a Cytoline 2 microcarrier), a Cytodex microcarrier (e.g. a Cytodex 1, Cytodex 2 or Cytodex 3 microcarrier), a Cytopore microcarrier (e.g. a Cytopore 1 microcarrier or a Cytopore 2 microcarrier), a Biosilon microcarrier, a Bioglass microcarrier, a FACT III microcarrier, a Collagen C microcarrier, a Hillex II microcarrier, a ProNectin F microcarrier, a Plastice microcarrier, a Plastic Plus microcarrier, a Nunc 2D MicroHex™ microcarrier, a Glass microcarrier (Sigma Aldrich), a DE 52/53 microcarrier or combinations thereof.

Microcarrier culture has significant advantages, including the scale-up of cultures, and also allows units of cells to be exposed to selected culture conditions as required in order to obtain the desired growth and/or differentiation conditions. The surfaces of the microcarriers may be further modified by physical or chemical treatments, such as adsorption or covalent cross-linking of molecular entities with a desired charge or other desired characteristic. The microcarrier may be complexed with a charged (e.g. negatively charged) tag. In other words, a microcarrier is provided that is conjugated or labelled with a charged (e.g. negatively charged) microsphere. The microcarrier may be complexed with a rod-shaped tag to form a microcarrier conjugated or labelled with a rod-shaped tag.

Kits according to the invention may comprise tags. Tags may be used as labels or tags which are conjugated to a microcarrier, such as a cell-associated microcarrier. Subsequent detection and identification provides for an unambiguous record of the chronology and identity of the cell culture conditions to which the cell unit has been exposed. Various molecular or macromolecular tags may be used in combination with the microcarriers so long as they can be detected. The tags typically comprise uniquely shaped or objects modified with markings and/or coloured and/or fluorescent compounds. In one embodiment the tags which are used to label cell units have one or more (preferably all) of the following qualities:

i. They are small in size relative to the microcarrier they are labelling and/or smaller than the mean pore size of a porous microcarrier;
  ii. They are capable of forming a complex with the microcarrier such that binding persists throughout the experiment and so unbound tags can be separated from the complex without affecting the labelled cell units;
  iii. They are separable from cell units with which they have formed a complex under conditions which do not perturb the unique qualities of the tags iv. They are made of one or more inert substances which do not substantially affect the biology of the cell unit and which in turn is not affected by the cell units or their biology;

v. They are obtainable in large numbers and moreover in many related but distinct variants which are easily distinguishable using an appropriate technique;

vi. They are distinguished by a method which is convenient, highly reliable and which can be automated.

In one embodiment, the tag is a microsphere—such as a fluorescent and/or coloured microsphere. More than 2000 different microspheres made by emulsion or suspension polymerization, precipitation etc. and comprised of polystyrene, other polymers, copolymers, terpolymers and/or silica etc. are available in a variety of sizes, densities, colours etc. A common type of microsphere is the Polystyrene (PS) and styrene/divinylbenzene copolymer (S/DVB) microsphere. Other polymers include polymethylmethacrylate (PMMA), polyvinyltoluene (PVT), styrene/butadiene (S/B) copolymer, styrene/vinyltoluene (S/VT) copolymer. Many of these microspheres can be functionalised, for instance by carboxyl groups as in the CML microspheres, or by amino functionalized or nitrogen-containing compounds, like primary, secondary, tertiary, and quaternary aliphatic amines, aromatic amines, and pyridines or sulfoxides which offer alternative coupling reactions to the COOH beads.

Suitably, the microsphere is a hydrophilic microsphere. More suitably the microsphere is a polystyrene microsphere. Most suitably, the microsphere is a surface-modified microsphere such as a carboxylate modified (CML) microsphere.

In one embodiment, one or more CML microspheres are complexed together with one or more microcarriers with positive charge. CML microspheres have a highly charged surface layer of carboxyl groups derived from a copolymerisation process. The surface is somewhat porous and relatively hydrophilic, but retains overall hydrophobic properties. The charge density of these particles ranges from about 10-125 $Å^2$ per carboxyl group, and they are stable to high concentrations of electrolytes (up to 1M univalent salt). The CML latex will adsorb proteins and other biomolecules, but much less strongly than hydrophobic microspheres.

In some embodiments, conjugates of microspheres and proteins, e.g. streptavidin are prepared. For example, conjugates with CML microspheres may be prepared as follows. CML microspheres may be activated using a water soluble carbodiimide reagent that makes the carboxyl groups reactive with primary amines on the proteins to be coupled. A 50 mM reaction buffer at pH 6.0 is prepared. Sodium acetate or 2-[N-morpholino]ethanesulfonic acid (MES) are suitable buffers. The protein is dissolved in the reaction buffer at a concentration of 10 mg/mL. A 1% (w/v) suspension of microspheres is prepared in the reaction buffer. One volume protein solution to ten volumes microsphere suspension is prepared and the mixture allowed to incubate, at room temperature for 20 minutes. A solution of 10 mg/mL (52 μMol/mL) of 1-ethyl-3-(3-dimethylaminopropyl)carbodiimide (EDAC) in deionized water is prepared and used immediately. A calculated amount of EDAC solution to the microsphere suspension is added and the pH of the reaction mixture adjusted to 6.5±0.2 with 0.1N NaOH. The mixture is incubated on a rocker or mixing wheel for 2 hours at room temperature. Unbound protein is removed and stored in storage buffer.

Advantageously, CML and other microspheres can be obtained in various formats—such as various colors (e.g. blue, red, green, yellow, black), various fluorophores (e.g. Pacific Blue (blue), Alexa Fluor® (blue), Fluorescein (green), Fluorescein (red), Firefli™ (red) Fluorescein (green), Fluorescein (red) or Fluorescein and Rhodamine (red green) and various sizes (e.g. 5.4 μm ($1.14×10^{10}$ beads/gram), and 7.6 μm ($4.10×10^9$ beads/gram)). CML and other microspheres may be prepared such that they are loaded with one or more visible dyes and/or fluorophores.

In one embodiment, tags, such as microspheres, are not coated with proteins.

Advantageously, CML microspheres not coated with proteins (e.g. streptavidin) are highly negatively charged and they adhere extremely tightly to microcarriers, which carry a positive charge. By varying various parameters in the fabrication process, commercial microsphere providers, such as Bangs Laboratories, can manufacture bead sets which can be distinguished based on differing sizes (e.g. bead sets of 4.4 μm and 5.5 μm diameter). Beads within each size group can be furthermore distinguished from each other based on differing fluorescence intensity owing to differential loading with a single fluorescent dye. It is possible to use many different dyes with different absorption or emission characteristics, which can be attached to the microcarriers described herein. Accordingly, tag diversity may result from varying tag size and/or fluorophore loading (i.e. fluor intensity) and/or fluorophore identity/combination. In particular, tag diversity may result from the type of fluorophore they carry (e.g. beads can be loaded with either UV2 or Starfire Red); size (e.g. for each fluorophore there are 5 different bead sizes: 1.87, 4.41, 5.78, 5.37 and 9.77 microns) and/or the quantity of fluorophore they carry (5 different intensities of each dye are available). Other fluorophores, such as TRITC, may be used. Filters can then be used to detect the at least 4 different dyes on any given bead—such as the TRITC filter (ex 540/25; dm 565; ba 605/55) for TRITC visualization from Nikon; the DAPI filter (ex 340-380; dm 400; ba 435-485) for UV2 visualization from Nikon; the GFP-B filter (ex 460-500; dm 505; ba 510-560) for FITC visualization from Nikon and the Cy5 filter set (cat no 41008 from Chroma Technology) for Strarfire Red visualization.

Microspheres can be dyed internally or externally, with visible or fluorescent dyes. Internal dyeing occurs when the dye is integrated into the microsphere mass, typically by soaking the microsphere in a solution containing a dye or fluorophore. External modification occurs when a dye is conjugated to the surface of the microsphere, for instance modification of a CML microsphere with an isothiocyanate derivative as described herein. Accordingly, in some embodiments, the microsphere may be dyed internally or externally, with visible or fluorescent dyes. It is furthermore possible to use 'quantum dots' to obtain a very high number of different fluorescent labels which can be read conveniently.

In one embodiment, flow cytometry may be used to determine the identity of one or more microspheres. Microspheres designed for use in flow cytometry readout are available in the art.

In certain embodiments, quantum dots are preferable due to the fact they do not fade (photo-bleach) when exposed to light. For instance the fluorophore FITC is known to photobleach and cell units treated with tags containing FITC are ideally handled in the dark and are difficult to analyse reliably. Quantum dots may be incorporated into microspheres at the time of polymerizing the polystyrene resulting in even loading of tags. Quantum dots are available in many colours and they can be excited at the same wavelength so allowing visualization of multiple colours without filters, by using a colour CCD camera. Further background information on Quantum dots is available from U.S. Pat. Nos. 6,322,901, 6,576,291, US2003/0017264, U.S. Pat. Nos. 6,423,551, 6,251,303, 6,319,426 6,426,513, 6,444,143, US2002/0045045, U.S. Pat. Nos. 5,990,479, 6,207,392, 6,251,303, 6,319,426, 6,426,513 and 6,444,143.

Advantageously, the tags are protected against degradation by the components of the cell culture, for example by chemical or other modification or by encapsulation. Encapsulation of tags can take place in many different media, for example in beads as already described herein-such as those from Bangs Laboratories Inc. (Fishers Ind., USA), and encapsulation may be used to standardise tag dosage in addition to providing components for tag amplification and/or detection (for example by providing PCR primers for use with a DNA tag). Detection of tags can be accomplished by a variety of methods familiar to those skilled in the art. Methods include mass spectrometry, nuclear magnetic resonance, sequencing, hybridisation, antigen detection, electrophoresis, spectroscopy, microscopy, image analysis, fluorescence detection, etc. In some embodiments, since the tags typically contain a colour or a fluorophore then flow cytometry, microscopy, spectroscopy, image analysis and/or fluorescence detection may be used.

The tags do not necessarily have to be distinguished by their chemical or molecular structure in the first instance. Multiple variations of the non-chemical tagging strategy can be devised to determine the identity of a given cell unit in a mixture or of deducing the identity of the different cell units that comprise a mixture. For instance optical or visual methods of tagging have been described where different shaped objects, graphically encoded objects or different colours denote the identity of a sample (for example see 1998, Guiles et al, Angew. Chem. Intl Ed Engl, vol. 37, p 926; Luminex Corp, Austin Tex., USA; BD Biosciences; Memobead Technologies, Ghent, Belgium). Suitably, the tag may be a charged tag (e.g. a negatively charged tag). Suitably, the tag may be complexed with a microcarrier—such as a porous microcarrier. Typically, the microcarrier has a net charge. Typically, the microcarrier and tag have opposite charges. The microcarrier may comprise, consist or consist essentially of protein, cellulose, polyethylene, polystyrol, glass collagen, collagengylcose-aminoglycan, gelatine, or derivatives thereof. The microcarrier may be selected from the group consisting of a Cultispher-G microcarrier, a Cultispher-GL microcarrier, a Cultispher-S microcarrier, an Informatrix microcarrier, a Microsphere microcarrier, a Siran microcarrier, a FibraCel® Disks microcarrier, a Cytoline microcarrier (e.g. a Cytoline 1 microcarrier or a Cytoline 2 microcarrier), a Cytodex microcarrier (e.g. a Cytodex 1, Cytodex 2 or Cytodex 3 microcarrier), a Cytopore microcarrier (e.g. a Cytopore 1 microcarrier or a Cytopore 2 microcarrier), a Biosilon microcarrier, a Bioglass microcarrier, a FACT III microcarrier, a Collagen C microcarrier, a Hillex II microcarrier, a ProNectin F microcarrier, a Plastice microcarrier, a Plastic Plus microcarrier, a Nunc 2D MicroHex™ microcarrier, a Glass microcarrier (Sigma Aldrich), a DE 52/53 microcarrier or combinations or derivatives thereof.

Suitably, the charged tag is a sphere—such as a microsphere, that is about <20 µm or less in diameter.

The microsphere may be a carboxylate modified (CML) microsphere. In a further embodiment, the tag is a rod-shaped particle. Suitably, the rod-shaped tag is a nanowire. The nanowire may comprise, consist or consist essentially of various metals—such as gold or silver. The nanowire may consist of different length segments made from various metals such as silver and/or gold. Suitably, the nanowire is about 1 µm or less in diameter and/or is about 10 µm or less in length. The nanowire may be a nanowire as described in Science vol. 294, p. 137-141 (2001). Accordingly, there is also described a complex comprising a microcarrier and a nanowire. Briefly, nanowires are multimetal microrods intrinsically encoded with submicrometer stripes. Complex patterns can be generated by sequential electrochemical deposition of metal ions onto templates with uniformly sized pores. Advantageously, the nanowires are small enough to be used as tags that may be added after each split. This is more convenient as it is necessary to read tags only in the positive microcarriers. Parameters for the rod-shaped particle—such as the nanowire—include but are not limited to size, optical properties and/or metal composition. In one embodiment, the optical properties are selected from the group consisting of: light reflectivity—such as light reflectivity of a particular wavelength, colour, the fluorescence emission wavelength(s) and the fluorescence emission intensity. In some embodiments, the rod-shaped particle—such as the nanowire is externally dyed. Microcarriers that can be used together with the rod-shaped tag are described herein.

Advantageously, it has been found that using rod shaped tags and charge-neutral porous microcarriers is better than using spherical tags on the same microcarriers. Without wishing to be bound by an particular theory it is believed that smaller tags penetrate the pores of the microcarriers better and become jammed (presumably due to size asymmetry). Accordingly, the binding of nanowires is better than, for example, the binding of microsphere tags and results in a high level permanent tagging. In another embodiment, one or more polystyrene microbeads are complexed together with one or more Cultispher-G microcarriers. For some embodiments, the tag is not a DNA tag. In some embodiments, the tag is an externally dyed tag.

In a further embodiment, the tags use radio waves to transmit information, as in RFID tags. RFID generally employs transponders (RF tags), antennae and readers. An RF tag is a small electronic circuit, usually encased in glass or plastic, which in its simplest form provides access to a unique identification code that may be 'read', without contact or line of sight, by suitable electronics. Tags may also store information generated by the user, again without contact or line of sight. A 'reader' is an electronic unit that transfers information to and from one or more tags (it should be noted that the term reader is used interchangeably to mean both a read only and read/write unit). The size and features of a reader may vary considerably, and it may operate in isolation, or be connected to a remote computer system. An antenna is used to transmit information from a reader to a tag, and to receive information sent by an RF tag. The size and format of an antenna will reflect the specific application, and may range from a small circular coil to large planar structures. An RFID system may operate in isolation, or be connected to a remote computer for more comprehensive interpretation and manipulation of identification and associated data derived from a tag. One RFID strategy is described in Nicolaou et al (1995, Angew Chem Intl Ed Engl, vol. 34, p. 2289) and comprises: (i) a porous enclosure containing a synthesis substrate and the semiconductor tag; (ii) the solid phase synthesis resin; (iii) a glass-encased Single or Multiple Addressable Radiofrequency Tag semiconductor unit capable of receiving, storing and emitting radiofrequency signals. A similar device could be adapted to growing and following cell units simply by replacing the solid phase synthesis resin with tissue culture microcarriers or suitable cell units. More variations of this can be envisaged including but not limited to (coated or uncoated) RF tags on which cells are grown directly, or RF tags implanted into cell units or organisms.

Groups of cells (cell colonies) can be grown in cell culture under various conditions and the colony can largely maintain its integrity under various conditions, when disturbed, and when mixed with other colonies. Such groups or colonies are referred to herein as cell units. Formation of cell units may be achieved, by way of illustration, by growing cells as adherent cultures on solid substrates such as carriers. If cell proliferation occurs after seeding on the carriers, the daughter cells will attach on the same carrier and form part of the same colony. In general, live adherent cells do not readily dissociate from their growth substrate, and so the integrity of the cell colony persists despite any mechanical manipulation of the carrier, agitation of the culture medium, or transfer into another tissue culture system. Similarly, if at any time multiple carriers are placed in the same vessel (e.g. beads are pooled) then there will be no substantial transfer of cells from one bead to another. An important advantage of forming cell units on solid substrates is that the substrate—and therefore the attached cells by reason of association—can be labelled as described herein. When cells are grown on smaller carriers they can be treated as a suspension culture. A common method of growing cells on small carriers is referred to as microcarrier cell culture (see 'Microcarrier cell culture, Principles and Methods', Edition AA, available from Amersham Biosciences (18-1140-62); herein incorporated in its entirety by reference). Microcarrier cultures are used commercially for antibody and interferon production in fermenters of up to 4000 liters. As the physical properties of carriers are well known it is easy to calculate the number of carriers used in an experiment.

The carriers may be available as dried products, which can be accurately weighed, and subsequently prepared by swelling in liquid medium. In addition the number of cells used to inoculate a microcarrier culture can be worked out and varied. Harvesting of cells grown on the microcarriers described herein, or liberation of labels from microcarriers, can be achieved by enzymatic detachment of cells, and/or by digestion of the carrier where applicable as described herein.

Any dimensions appearing in the Figures are of currently preferred embodiments and are not to be understood as limiting on the scope of the present invention.

The invention is further described by the following numbered paragraphs:

1. An apparatus for culturing cells comprising two or more culture compartments and a pooling compartment, wherein:
   each of said two or more culture compartments is separated from the other culture compartments;
   each of said two or more culture compartments comprises a port for the addition or removal of medium; and
   the pooling compartment communicates with said two or more culture compartments.

2. An apparatus according to paragraph 1, wherein cell cultures present in the two or more culture compartments can be combined by being transferred into the pooling compartment.

3. An apparatus according to paragraph 1, wherein a cell culture present in the pooling compartment can be split by being transferred into the culture compartments.

4. An apparatus according to any preceding paragraph, wherein cell cultures can be transferred between the culture compartments and the pooling compartment by tilting the apparatus.

5. An apparatus according to any preceding paragraph, wherein the port present in each culture compartment comprises a filter to allow removal of any one or more of culture medium, tags and cells which have become dissociated from cell units, whilst retaining cell units within the compartment.

6. An apparatus according to any preceding paragraph, which comprises, in addition to said ports, one or more routes for the addition or removal of medium.

7. An apparatus for culturing cells, comprising: a plurality of culture compartments, isolated from one another by a separator wall, at least two of said culture compartments being joined to a pooling compartment at one end of said culture compartments; such that, when the apparatus is tilted in the direction of the pooling compartment, culture medium flows from the parallel compartments into the pooling compartment, and media from said two or more compartments are pooled; and when the apparatus is tilted in the direction of the culture compartments, culture medium in the pooling compartment is divided into said two or more culture compartments, separated by the separator wall; and wherein each culture compartment comprises a port for the addition or removal of medium.

8. An apparatus according to paragraph 8, wherein the culture compartments are arranged substantially parallel with each other in the vessel.

9. An apparatus according to any preceding paragraph, which is constructed from a material selected from the group consisting of polyethylene, polypropylene, polyvinylchloride, polycarbonate, polystyrene, polyester, nylon, aramid polymers and a metal, or combinations thereof.

10. An apparatus according to any preceding paragraph, which is at least partly optically transparent.

11. An apparatus according to any preceding paragraph, comprising a dust shield or lid at least partially covering some or all of the compartments.

12. A method for repeated splitting and pooling of a culture of cells, comprising the steps of:
   (a) providing one or more cultures of cells and distributing the cultures between two or more culture compartments of an apparatus according to any preceding paragraph;
   (b) optionally, adding and/or removing one or more media reagents, which may be the same or different, to or from one or more of said two or more compartments, and/or culturing the cells;
   (c) pooling the cell cultures in the pooling compartment, to create a pooled cell culture;
   (d) splitting said pooled cell culture by distributing the pooled culture into the culture compartments; and
   (e) optionally, repeating one or more of steps (b)-(d).

13. A method according to paragraph 12, further comprising the step of isolating the cells from one or more of said compartments.

14. The method of paragraph 12 or paragraph 13, comprising culturing the cells, wherein the step of culturing the cells comprises the following sub-steps: (i) transferring the cells from said two or more compartments to one or more different containers; (ii) culturing the cells in said one or more containers; and (iii) optionally, returning the cells to an apparatus according to any one of paragraphs 1 to 11.

15. The method of paragraph 12 or paragraph 13, comprising culturing the cells in said two or more compartments of the apparatus.

16. A kit comprising an apparatus according to any one of paragraphs 1 to 11, one or more microcarriers and optionally one or more tags.

17. A kit according to paragraph 16, wherein said tags are used for labelling microcarriers and/or for labelling cells.

18. A kit according to paragraph 16 or paragraph 17, further comprising cells and/or cell culture or washing media.

19. A stand for apparatus of any one of paragraphs 1 to 11, the stand comprising support means for supporting the apparatus in at least first and second orientations, wherein said first and second orientations are angularly offset from each other.

20. A stand of paragraph 19 further comprising a first pair of cooperating slots for supporting the apparatus in said first orientation and a second pair of cooperating slots for supporting the apparatus in said second orientation; or a stand of paragraph 16, wherein said support means is adapted movably to support the apparatus to enable the apparatus to move from said first position to said second position.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. An apparatus for culturing cells, comprising:
   a plurality of culture compartments, isolated from one another by one or more separator walls, at least two of said culture compartments being joined to a in fluid communication with a pooling compartment at one end of said culture compartments; wherein said apparatus is constructed and arranged such that:
   in a first orientation of said apparatus, said pooling compartment is located below said culture compartments whereby liquid contents in said at least two culture compartments will flow into said pooling compartment to pool the liquid contents of said at least two culture compartments,
   in a second orientation of said apparatus, said pooling compartment is located above said culture compartments whereby liquid contents in said pooling compartment will flow into said at least two culture compartments for splitting liquid contents of said pooling compartment into said at least two culture compartments, and
   in said second orientation, cultures of cell units in each of said culture compartments may be exposed to differing culture conditions, in isolation, wherein said apparatus is in the form of a U-shaped vessel comprising first and second arms and an arcuate portion joining the first and second arms, wherein the bottom extends arcuately in said U-shape and the walls extend inwardly from said bottom in said first arm and arcuately in the curved portion of the vessel, such that the culture compartments are present in the first arm of the vessel and the pooling compartment exists in the second arm of the vessel.

2. An apparatus for culturing cells comprising two or more culture compartments and a pooling compartment, wherein:
   said apparatus comprises a first end and a second end and a bottom extending from said first end to said second end, one or more walls projecting from said bottom and extending from said first end of the apparatus to positions intermediate the first and second ends to define said two or more culture compartments, each of said two or more culture compartments is being separated from the other culture compartments by said one or more walls, and each of said two or more culture compartments having a channel shape having an open end located intermediate said first and second ends of the apparatus;
   each of said two or more culture compartments comprises a port for the addition or removal of medium; and
   the pooling compartment is positioned intermediate said second end of the apparatus and said open ends of said channel-shaped culture compartments and communicates with said open ends of said two or more culture compartments, wherein said apparatus is in the form of a U-shaped vessel comprising first and second arms and an arcuate portion joining the first and second arms, wherein the bottom extends arcuately in said U-shape and the walls extend inwardly from said bottom in said first arm and arcuately in the curved portion of the vessel, such that the culture compartments are present in the first arm of the vessel and the pooling compartment exists in the second arm of the vessel.

3. An apparatus according to claim 1, wherein the culture compartments are arranged substantially parallel with each other in the vessel.

4. An apparatus according to claim 2 or claim 1, which is constructed from a material selected from the group consisting of polyethylene, polypropylene, polyvinylchloride, polycarbonate, polystyrene, polyester, nylon, aramid polymers and a metal, or combinations thereof.

5. An apparatus according to claim 2 or claim 1, which is at least partly optically transparent.

6. An apparatus according to claim 2 or claim 1, comprising a dust shield or lid at least partially covering some or all of the compartments.

7. A kit comprising an apparatus according to claim 2 or claim 1, one or more microcarriers and optionally one or more tags.

8. A kit according to claim 7, wherein said tags are used for labelling microcarriers and/or for labelling cells.

9. A kit according to claim 7, further comprising cells and/or cell culture or washing media.

10. An apparatus according to claim 2, wherein the port present in each culture compartment comprises a filter to allow removal of any one or more of culture medium, and cells which have become dissociated from cell units, whilst retaining cell units within the compartment.

11. An apparatus according to claim 2, which comprises, in addition to said ports, one or more routes for the addition or removal of medium.

\* \* \* \* \*

UNITED STATES PATENT AND TRADEMARK OFFICE
CERTIFICATE OF CORRECTION

PATENT NO. : 9,017,998 B2  Page 1 of 1
APPLICATION NO. : 13/371543
DATED : April 28, 2015
INVENTOR(S) : Tarunina et al.

It is certified that error appears in the above-identified patent and that said Letters Patent is hereby corrected as shown below:

In the Claims

Col. 21, Claim 1, Line 3 change "wails" to --walls--

Signed and Sealed this
Fifteenth Day of September, 2015

Michelle K. Lee
*Director of the United States Patent and Trademark Office*